(12) United States Patent
Shirai et al.

(10) Patent No.: US 10,605,881 B2
(45) Date of Patent: Mar. 31, 2020

(54) MAGNETIC RESONANCE IMAGING APPARATUS AND IMAGE PROCESSING METHOD

(71) Applicant: Hitachi, Ltd., Tokyo (JP)

(72) Inventors: Toru Shirai, Tokyo (JP); Ryota Satoh, Tokyo (JP); Yo Taniguchi, Tokyo (JP); Hisaaki Ochi, Tokyo (JP); Takenori Murase, Tokyo (JP); Yoshitaka Bito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/088,912

(22) PCT Filed: Mar. 17, 2017

(86) PCT No.: PCT/JP2017/011032
§ 371 (c)(1),
(2) Date: Sep. 27, 2018

(87) PCT Pub. No.: WO2017/175570
PCT Pub. Date: Oct. 12, 2017

(65) Prior Publication Data
US 2019/0128991 A1    May 2, 2019

(30) Foreign Application Priority Data
Apr. 4, 2016  (JP) ................. 2016-075014

(51) Int. Cl.
*G01R 33/565* (2006.01)
*A61B 5/055* (2006.01)
(Continued)

(52) U.S. Cl.
CPC ........ *G01R 33/56536* (2013.01); *A61B 5/055* (2013.01); *G01R 33/443* (2013.01);
(Continued)

(58) Field of Classification Search
CPC ................ G01R 33/46; G01R 33/4608; G01R 33/4616; G01R 33/4625; G01R 33/4633;
(Continued)

(56) References Cited

U.S. PATENT DOCUMENTS

2012/0321162 A1   12/2012   Liu et al.
2013/0221961 A1   8/2013   Liu
(Continued)

FOREIGN PATENT DOCUMENTS

JP   2000-300535 A   10/2000
JP   2015-062637 A   4/2015
(Continued)

OTHER PUBLICATIONS

Tian Liu, et al., "Nonlinear Formulation of the Magnetic Field to Source Relationship for Robust Quantitative Susceptibility Mapping", Magnetic Resonance in Medicine, Feb. 2013, vol. 69, Issue 2, p. 467-476.
(Continued)

*Primary Examiner* — Tung X Nguyen
(74) *Attorney, Agent, or Firm* — Mattingly & Malur, PC

(57) ABSTRACT

In calculating a local magnetic field distribution caused by a magnetic susceptibility difference between living tissues, using MRI, a local frequency distribution with a high SNR is calculated in a short computation time. Multi-echo complex images obtained by measurement of at least two different echo times using the MRI are converted into low-resolution images. A global frequency distribution caused by global magnetic field changes and an offset phase distribution including a reception phase and a transmission phase are separated from a phase distribution of the low-resolution multi-echo complex images. Thus calculated global frequency distribution and the offset phase distribution are enhanced in resolution. A local frequency distribu-
(Continued)

tion of each echo is calculated from the measured multi-echo complex images, the high-resolution global frequency distribution, and the high-resolution offset phase distribution. The local frequency distributions of respective echoes are subjected to weighted averaging, whereby a final local frequency distribution is calculated.

12 Claims, 13 Drawing Sheets

(51) Int. Cl.
*G01R 33/56* (2006.01)
*G01R 33/44* (2006.01)
*G01R 33/48* (2006.01)
*G01R 33/561* (2006.01)

(52) U.S. Cl.
CPC ......... *G01R 33/4822* (2013.01); *G01R 33/56* (2013.01); *G01R 33/5602* (2013.01); *G01R 33/5611* (2013.01); *G01R 33/5616* (2013.01); *G01R 33/56545* (2013.01)

(58) Field of Classification Search
CPC .............. G01R 33/4641; G01R 33/465; G01R 33/543; G01R 33/56; G01R 33/5602; G01R 33/5604; G01R 33/5605; G01R 33/5607; G01R 33/5608; G01R 33/561; G01R 33/5611; G01R 33/5612; G01R 33/5613; G01R 33/5614; G01R 33/5615; G01R 33/5616; G01R 33/5617; G01R 33/5618; G01R 33/5619; G01R 33/563
See application file for complete search history.

(56) References Cited

U.S. PATENT DOCUMENTS

| | | |
|---|---|---|
| 2014/0210467 A1 | 7/2014 | Hwang et al. |
| 2014/0347052 A1* | 11/2014 | Kamata ............ G01R 33/56563 324/309 |
| 2015/0035530 A1* | 2/2015 | Tisdall ................ A61B 5/7285 324/307 |
| 2015/0084628 A1 | 3/2015 | Sato et al. |
| 2015/0145515 A1 | 5/2015 | Liu |
| 2015/0310639 A1 | 10/2015 | Bilgic et al. |
| 2015/0362575 A1 | 12/2015 | Ourselin et al. |
| 2017/0192075 A1* | 7/2017 | Nakai ................ G01R 33/4828 |

FOREIGN PATENT DOCUMENTS

| | | |
|---|---|---|
| WO | 2013/054718 A1 | 4/2013 |
| WO | 2014/057716 A1 | 4/2014 |
| WO | 2014/076808 A1 | 5/2014 |
| WO | 2015/161386 A1 | 10/2015 |

OTHER PUBLICATIONS

Berkin Bilgic, MRI estimates of brain iron concentration in normal aging using quantitative susceptibility mapping, Neuro Image, Feb. 2012, vol. 59, Issue 3, p. 2625-2635.
Tian Liu, et al., "A novel background field removal method for MRI using projection onto dipole fields (PDF)", NMR in Biomedicine, Nov. 2011, vol. 24, No. 9, p. 1129-1136.
Yi Wang, et al., "Quantitative Susceptibility Mapping(QSM): Decoding MRI Data for a Tissue Magnetic Biomarker", Magnetic Resonance in Medicine, Jan. 2015, vol. 73, Issue 1, p. 82-101.
International Search Report of PCT/JP2017/011032 dated Jun. 6, 2017.
International Preliminary Report on Patentability received in corresponding International Application No. PCT/JP2017/011032 dated Oct. 18, 2018.

* cited by examiner

FIG.1
(a)
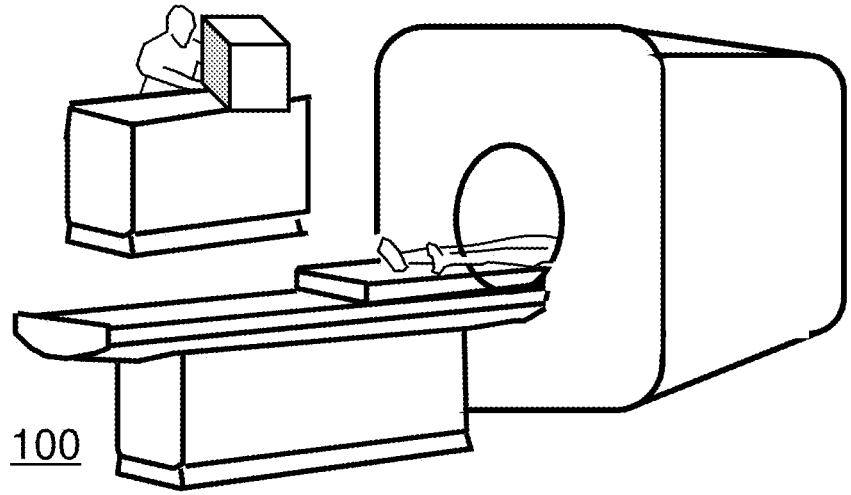
100
(b)
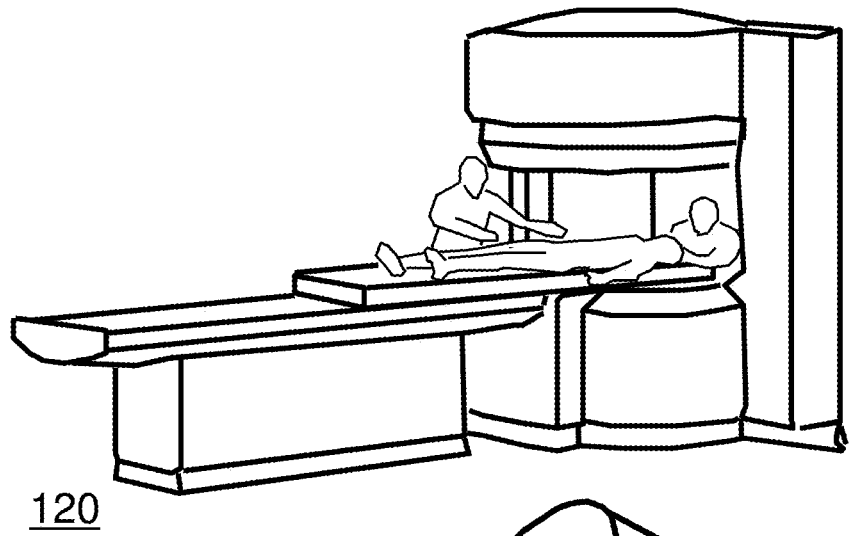
120
(c)
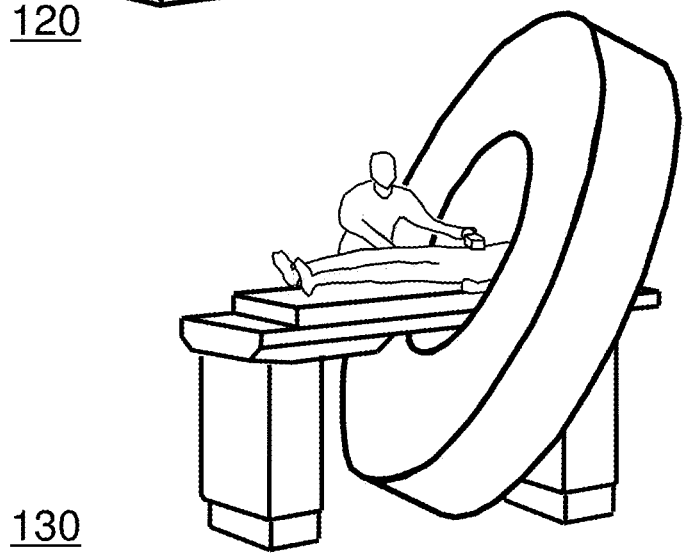
130

MAGNETIC RESONANCE IMAGING APPARATUS AND IMAGE PROCESSING METHOD

TECHNICAL FIELD

The present invention relates to a magnetic resonance imaging (hereinafter, referred to as "MRI") technique. In particular, it relates to an image processing technique that uses multi-echo complex images acquired at two or more different echo times, so as to calculate a distribution of local magnetic field changes caused by a magnetic susceptibility difference in tissues from a living body.

BACKGROUND ART

An MRI apparatus is a medical-use diagnostic noninvasive imaging apparatus, utilizing nuclear magnetic resonance phenomenon. The nuclear magnetic resonance phenomenon indicates that hydrogen nucleus (protons) placed in a static magnetic field, are resonant with an RF magnetic field at a specific frequency. Since nuclear magnetic resonance signals are changed depending on various physical properties, such as proton density and relaxation time, an image obtained by the MRI can depict various biological information items, such as a structure or a composition of living tissue and cell properties.

In recent years, a magnetic susceptibility difference between living tissues receives attention, as one of the physical properties being measurable by the MRI. The magnetic susceptibility is a physical property that represents a degree of magnetic polarization (magnetization) of materials in the static magnetic field. In a living body, there are contained paramagnetic substances such as deoxyhemoglobin and iron protein in venous blood, and diamagnetic substances such as water constituting a large part of the living tissue and calcium serving as a basis of calcification. Creating an image quantitatively from a magnetic susceptibility difference between the living tissues, or the magnetic susceptibility difference being weighted, may be applicable to diagnosis of cerebral ischemia disease, prediction of radiation treatment effect against cancer, and identification of neurodegenerative disease.

A method for creating an image of the magnetic susceptibility difference between living tissues by utilizing the MRI is referred to as quantitative susceptibility mapping (QSM). A method for creating an image by weighting the magnetic susceptibility difference between living tissues is referred to as susceptibility weighted imaging (SWI). The QSM is a method of calculating local magnetic field changes caused by the magnetic susceptibility difference between living tissues, from phase information of an MR image being measured, and obtaining a quantitative susceptibility distribution according to a relational expression between the magnetic field and the magnetic susceptibility. The SWI is a method of calculating a weighting mask image where local magnetic field changes are weighted, and multiplying a measured weighted image (absolute value image) by thus calculated weighting mask, thereby obtaining an image where the magnetic susceptibility is weighted.

In order to obtain the quantitative susceptibility distribution or the susceptibility weighted image, according to the QSM or the SWI, it is necessary to calculate the local magnetic field changes that are caused by the magnetic susceptibility difference between living tissues. Usually, by using the Gradient echo (GrE) method, a distribution of the local magnetic field changes (local magnetic field distribution) is calculated from a phase distribution that is measured at one echo time (TE). Specifically, the phase distribution is calculated from a measured complex image, a phase aliasing removal process is performed for removing phase aliasing that occurs within the range from −n to +n in thus calculated phase distribution. Thereafter, a background removal process is performed for removing global magnetic field (background magnetic field) changes caused by a subject shape or other factors, thereby obtaining the local magnetic field that is caused by the magnetic susceptibility difference between living tissues.

An image quality of the local magnetic field distribution depends on a signal-to-noise ratio (SNR: Signal Noise Ratio) of the measured phase distribution. It is known that in the phase distribution of MRI, the SNR of the phase distribution is maximized when measurement is performed at the TE corresponding to an apparent transverse magnetization relaxation time $T_2^*$ of the living tissue being a target. On the other hand, in the phase aliasing removal process, it is not possible to increase the length of TE, so as to remove the phase aliased over the range from −n to +n without fail. Accordingly, a phase distribution with an optimum SNR cannot be acquired if the TE is only one. In view of this, multi-echo measurement for acquiring images at a plurality of TEs allows obtaining the local magnetic field distribution with an optimum SNR, without failing in removing the phase aliasing.

There are suggested several methods for calculating the local magnetic field distribution from the phase distributions at a plurality of TEs obtained by the multi-echo measurement.

As representative methods, there are two methods as the following.

In one of the two methods (referred to as conventional method 1), in the phase distribution of the multi-echo images measured at a plurality of TEs, a phase aliasing removal process in the time direction is performed. Then, linear fitting is applied using a feature that the phase in the time direction varies linearly, thereby calculating a frequency component caused by static magnetic field inhomogeneity. Next, spatial frequency aliasing removal process is performed, followed by the background removal process, and a local magnetic field distribution is obtained (e.g., see Non Patent Document 1).

In the other method (referred to as conventional method 2), in the phase distribution of the multi-echo images measured at a plurality of TEs, the phase aliasing removal process and the background removal process are performed for the phase distribution of each echo individually, thereby obtaining the local magnetic field distribution of each echo. Then, weighted averaging is applied to the local magnetic field distributions of the respective echoes, so as to obtain a final local magnetic field distribution (e.g., see Patent Document 1).

PRIOR ART DOCUMENT

Non Patent Document

Non Patent Document 1
Liu T, et al., "Nonlinear Formulation of the Magnetic Field to Source Relationship for Robust Quantitative Susceptibility Mapping", Magnetic Resonance in Medicine, 2013, vol. 69, pp. 467-476

Patent Document

Patent Document 1
U.S. Unexamined Patent Application Publication No. 2012/0321162, DESCRIPTION

DISCLOSURE OF THE INVENTION

Problems to be Solved by the Invention

The conventional method 1 has an advantage that the phase aliasing can be removed with precision, since the phase aliasing removal is performed in the time direction. However, the phase linear fitting process is to be applied to each pixel, resulting in that a computation time becomes longer along with increase of the number of pixels. In addition, there is another issue that due to noise impact, the SNR of the obtained local magnetic field distribution tends to be low.

The conventional method 2 has an advantage that the SNR of the calculated local magnetic field is improved, since weighted averaging is applied to the local magnetic field distributions of the respective echoes. However, the background removal process has to be performed on each echo image, resulting in that the computation time becomes longer along with the increase of the number of echoes. In addition, there is another issue that phase aliasing removal may become inaccurate in a region where a difference of the magnetic susceptibility between living tissues is large, in the case of an echo image measured with a long TE.

The present invention has been made in view of the situations above, and an object of the present invention is to provide a method for obtaining a local frequency distribution with a short computation time and high SNR, in calculating a local magnetic field distribution caused by a magnetic susceptibility difference between living tissues, with the use of the measured data obtained in the MRI.

Means for Solving the Problems

In the present invention, multi-echo complex images measured at different echo times at least two, using an MRI, are converted into low-resolution images. A global frequency distribution caused by a global magnetic field change and an offset phase distribution including phases such as a reception phase and a transmission phase, are separated from a phase distribution of the low-resolution multi-echo complex images. Thus obtained global frequency distribution and the offset phase distribution are enhanced in resolution. A local frequency distribution of each echo is obtained, from the measured multi-echo complex images, the high-resolution global frequency distribution, and the high-resolution offset phase distribution. Weighted averaging is applied to the local frequency distributions of the respective echoes, and a final local frequency distribution is calculated.

Advantage of the Invention

In calculating the local magnetic field distribution caused by the magnetic susceptibility differencebetweenlivingtissues, with the use of MRI, the local frequency distribution with a short computation time and high SNR can be obtained.

BRIEF DESCRIPTION OF THE DRAWINGS

FIGS. 1(a) to 1(c) are external views of an MRI apparatus to which the present invention is applied;

BEST MODE FOR CARRYING OUT THE INVENTION

Figure 2:
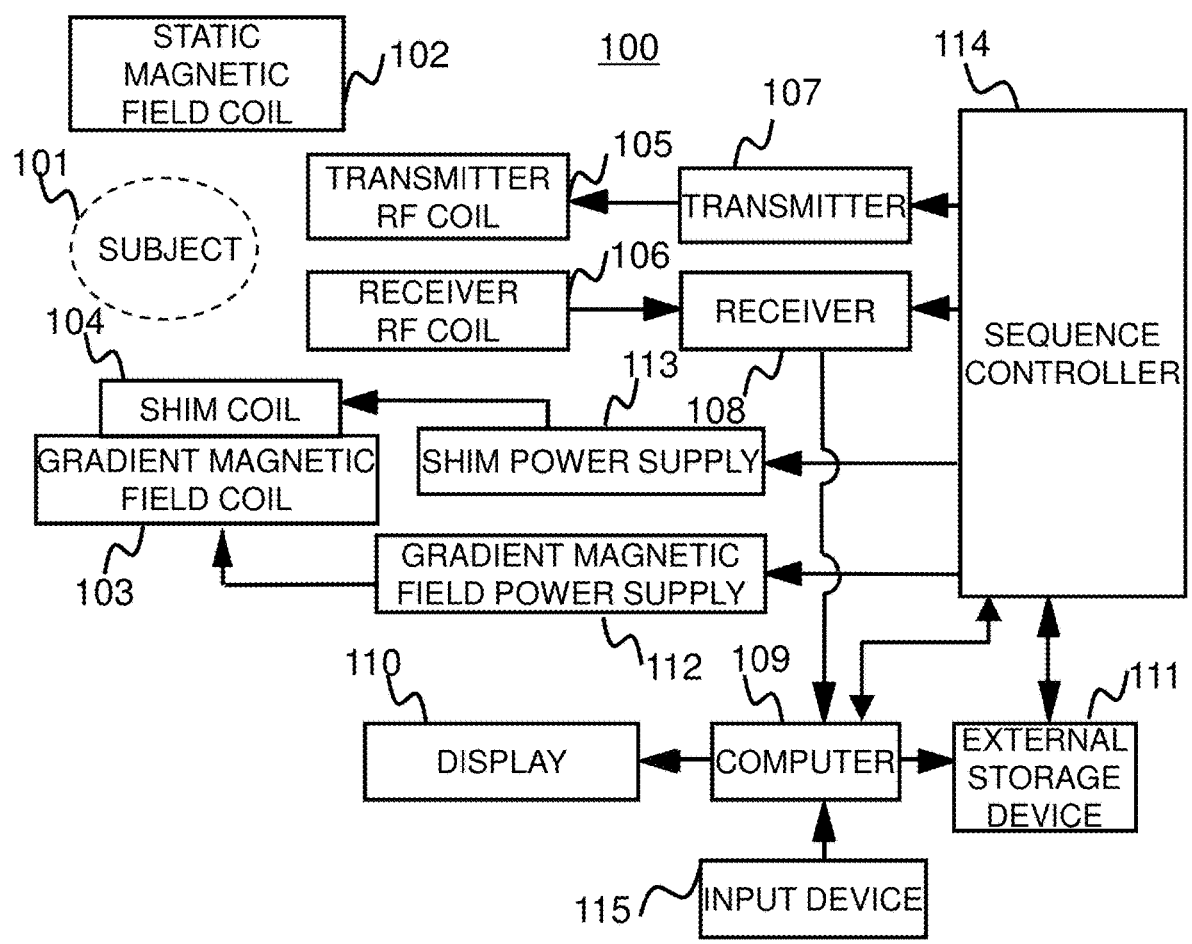
FIG. 2 illustrates one embodiment of a configuration of the MRI apparatus.

Embodiments to which the present invention is applied will now be described. Hereinafter, in all the figures illustrating the embodiments of the present invention, elements with an identical function are labeled with the same reference numeral, unless otherwise specified, and they will not be redundantly explained.

First Embodiment

<External View of MRI Apparatus>

Firstly, an embodiment of an MRI apparatus to which an aspect of the present invention is applied will be described. FIGS. 1(a) to 1(c) are external views of the MRI apparatus. FIG. 1(a) illustrates the MRI apparatus 100 of the horizontal magnetic field type that uses a tunnel-type magnet for generating a static magnetic field by a solenoid coil. FIG. 1(b) illustrates the MRI apparatus 120 of a hamburger-type (open-type) vertical magnetic field system in which the magnets are separated vertically so as to enhance a sense of openness. FIG. 1(c) illustrates the MRI apparatus 130 of the same tunnel-type as FIG. 1(a), using a magnet with reduced depth and put in a slanting position, thereby enhancing the sense of openness.

The present embodiment may employ any types of the MRI apparatus having those external views as described above. It should be noted that these are a few examples, and the MRI apparatus of the present embodiment is not limited to those examples shown here. In the present embodiment, various publicly-known MRI apparatuses may be employed, including any mode or any type thereof. In the following, the MRI apparatus 100 will be taken as a representative example, unless otherwise distinguished.

[Configuration of the MRI Apparatus]

FIG. 2 is a functional block diagram of the MRI apparatus 100 according to the present embodiment. As illustrated, the MRI apparatus 100 of the present embodiment is provided with a static magnetic field coil 102, including, for example, a coil for a static magnetic field and a magnet for generating the static magnetic field, and others, configured to generate a static magnetic field in the space where a subject 101 is placed, a shim coil 104 for adjusting a static magnetic field distribution, a transmitter RF coil 105 (hereinafter, simply referred to as "transmitter coil") for transmitting an RF magnetic field to a measurement region of the subject 101, a receiver RF coil 106 (hereinafter, simply referred to as "receiver coil") for receiving nuclear magnetic resonance signals generated from the subject 101, a gradient coil 103 for applying a gradient magnetic field to each of the directions; x-direction, y-direction, and z-direction, so as to add positional information to the nuclear magnetic resonance signals generated from the subject 101, a transmitter 107, a receiver 108, a computer 109, a gradient magnetic field power supply 112, a shim power supply 113, and a sequence controller 114.

Various types of the static magnetic field coil 102 may be employed, in response to the structures of the MRI apparatuses 100, 120, and 130 as shown in FIGS. 1(a), 1(b), and 1(c), respectively.

A transmitter 107 generates an RF magnetic field that is emitted from the transmitter coil 105. That is, the transmitter coil 105 and the transmitter 107 function as a transmission unit. A nuclear magnetic resonance signal detected by the receiver coil 106 is transferred to the computer 109 via a receiver 108. That is, the receiver coil 106 and the receiver 108 function as a reception unit. In FIG. 2, there is described the case where the transmitter coil 105 and the receiver coil 106 separately provided are used. However, it is possible to configure such that one coil is employed, which serves both functions; the transmitter coil 105 and the receiver coil 106.

The gradient coil 103 and the shim coil 104 are driven by the gradient magnetic field power supply 112 and the shim power supply 113, respectively. The gradient coil 103 and the gradient magnetic field power supply 112 function as a gradient magnetic field generator.

The sequence controller 114 controls operations of the gradient magnetic field power supply 112 being a power source for driving the gradient coil 103, the shim power supply 113 being a power source for driving the shim coil 104, the transmitter 107, and the receiver 108, thereby controlling application of the gradient magnetic field and the RF magnetic field, and receiving timing of the nuclear magnetic resonance signal. A time chart of the control is referred to as a pulse sequence, whose settings are previously configured depending on the measurement, and it is stored, for example, in a storage device being provided in the computer 109 as described below.

The computer 109 controls the entire operation of the MRI apparatus 100, along with performing various computations on the nuclear magnetic resonance signals being received. In the present embodiment, the computer generates complex images of at least two echo times, a phase distribution, a magnetic field distribution, a magnetic susceptibility distribution, and a susceptibility weighted image, and the like. The computer 109 is an information processor including a CPU, a memory, and a storage device, and the computer 109 is connected to other devices, such as a display 110, an external storage device 111, and an input device 115.

The display 110 is an interface for an operator, configured to display information such as a result obtained by computations. The input device 115 is an interface configured to allow the operator to input conditions, parameters, and the like, necessary for the measurement and computations performed in the present embodiment. The input device 115 of the present embodiment allows the user to input measurement parameters, such as the number of echoes to be measured, a reference echo time, and an echo interval. The external storage device 111, along with the storage device within the computer 109, holds data such as the data used in various computations executed by the computer 109, data obtained through the computations, conditions and parameters being inputted.

[Configuration of the Computer]

In the MRI of the present embodiment, the computer 109 uses a complex image to perform computations for generating a magnetic field distribution, a magnetic susceptibility distribution, a susceptibility weighted image, and the like. Next, there will be described a configuration example of the computer 109 that implements such computations.

Figure 3:
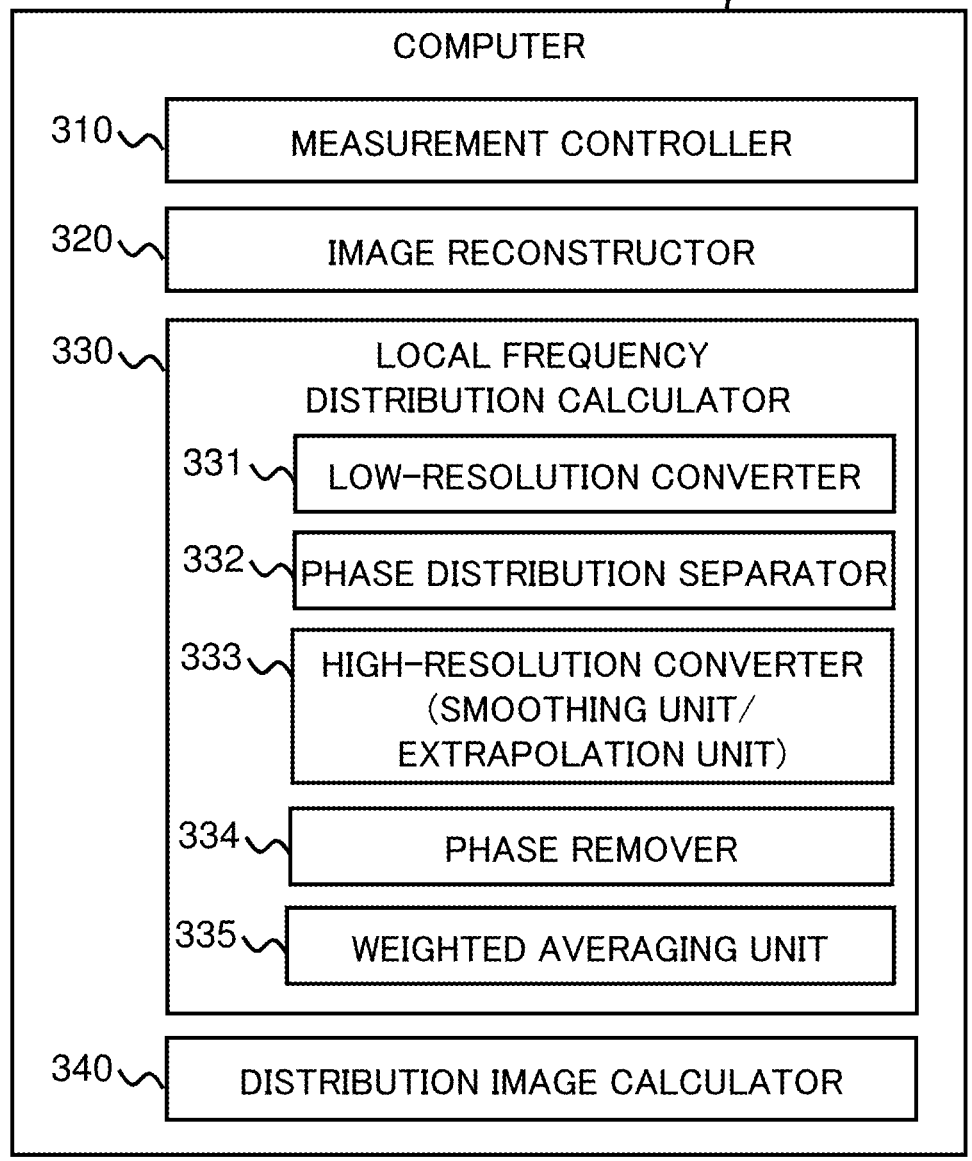
FIG. 3 is a functional block diagram of a computer according to a first embodiment.

FIG. 3 is a functional block diagram of the computer 109 according to the present embodiment. The computer 109 of the present embodiment includes, a measurement controller 310 configured to measure complex signals of nuclear magnetic resonance signals (echo signals) of at least two different echo times, generated from the subject in response to irradiation of RF magnetic field pulses, an image reconstructor 320 configured to reconstruct a complex image where a pixel value is a complex value, from the complex signals measured by the measurement controller 310, a local frequency distribution calculator 330 configured to calculate a local frequency distribution from the complex image reconstructed by the image reconstructor 320, and a distribution image calculator 340 configured to calculate a distribution image aiming at obtaining a quantitative susceptibility distribution, a susceptibility weighted image, and the like, from the local frequency distribution calculated by the local frequency distribution calculator 330. Details of the local frequency distribution calculator 330 will be described later.

A CPU loads programs (software) held in the storage device into a memory and executes those programs, whereby those functions of the elements in the aforementioned computer 109 are implemented. The storage device or the external storage device 111 may store various data used for processing of the functions, and various data generated in process. Another information processor that is independent of the MRI apparatus 100, data transmittable and receivable thereto and therefrom, may implement at least one of the various functions implemented by the computer 109. Furthermore, all or a part of the functions may be implemented by hardware such as ASIC (Application Specific Integrated Circuit) and FPGA (Field-Programmable Gate Array).

[Processing of the Computer]

In the light of the configuration of the computer 109 as described above, an overview of the processing performed by the computer 109 will be described with reference to FIG. 4.

Firstly, the measurement controller 310 controls the sequence controller 114 according to a predetermined pulse sequence, thereby measuring echo signals of at least two different preset echo times (step S1001).

Then, the image reconstructor 320 places thus obtained echo signals in k-space, applies Fourier transform thereto, thereby reconstructing complex images I(n) (step S1002). Accordingly, multi-echo complex images comprising complex images of different echo times, respectively, can be obtained.

The local frequency distribution calculator 330 performs a local frequency distribution calculation process that calculates a local frequency distribution from the complex images (step S1003).

Thereafter, the distribution image calculator 340 performs processing for calculating desired distribution images from thus calculated local frequency distribution, such as the quantitative susceptibility distribution and the susceptibility weighted image (step S1004), and displays the calculated distribution images on the display 110 (step S1005).

When the distribution images such as the quantitative susceptibility distribution and the susceptibility weighted image are displayed on the display 110, other images obtained in the process of any desired distribution calculation may be displayed on the display 110 as appropriate, in addition to the local frequency distribution and others as calculated in the step S1003.

Next, details of each process will be described.

[Measurement: S1001]

The measurement controller 310 activates the sequence controller 114, according to the pulse sequence that is configured on the basis of the parameters inputted by a user via the input device 115, and performs measurement so as to obtain a nuclear magnetic resonance signal (echo signal) at a preset echo time (TE). The sequence controller 114 controls each component of the MRI apparatus 100 according to the instructions from the measurement controller 310 to perform the measurement. In the present embodiment, echo signals of at least two echo times (N times) are obtained.

An example of the pulse sequence used by the measurement controller 310 for the measurement will be described. By way of example, in the present embodiment, a pulse sequence of GrE (Gradient Echo) system may be employed. The pulse sequence of this GrE system is sensitive to local magnetic field changes arisen from magnetic susceptibility differences between living tissues.

Figure 5:
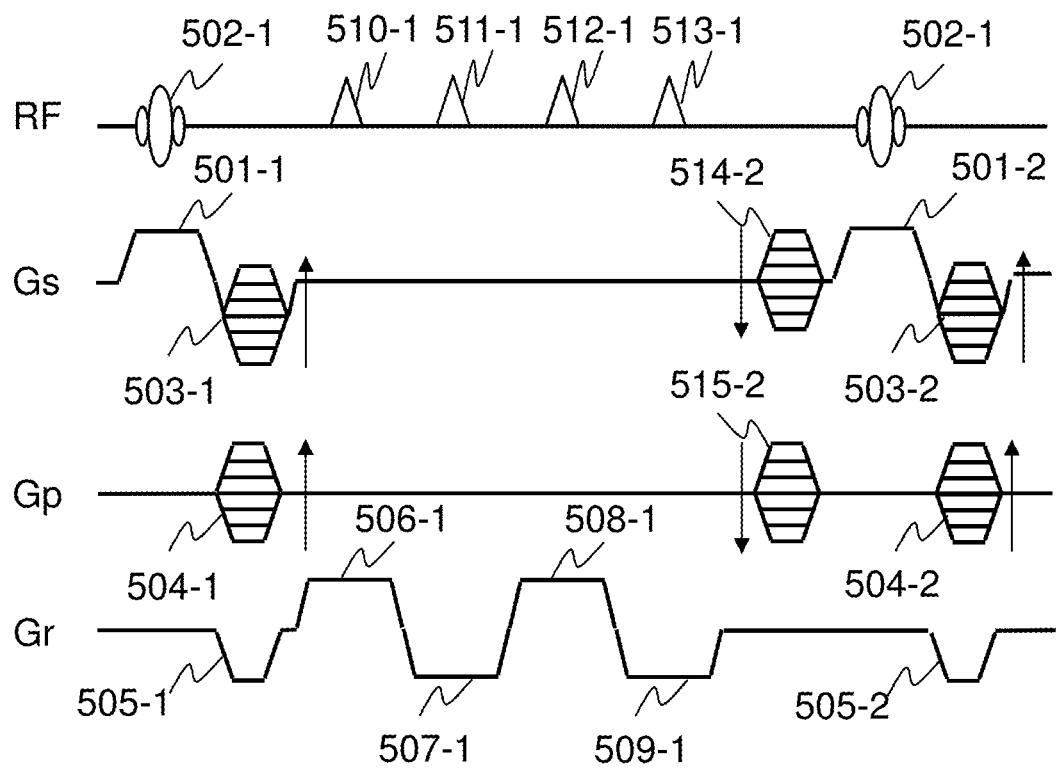
FIG. 5 illustrates an example of a pulse sequence used for acquiring data of a complex image.

FIG. 5 Illustrates an RSSG (RF-spoiled-Steady-state Acquisition with Rewound Gradient-Echo)-Multiecho sequence 550, as an example of the GrE-system pulse sequence. In this figure, RF, Gs, Gp, and Gr represent, respectively, an RF magnetic field, a slice gradient magnetic field, a phase encoding gradient magnetic field, and a readout gradient magnetic field.

In the RSSG sequence 550, a radio-frequency (RF) magnetic field pulse 502 is applied along with application of a slice gradient magnetic field pulse 501, thereby exciting magnetization of a predetermined slice within the subject 101. Then, a slice encoding gradient magnetic field pulse 503 and a phase encoding gradient magnetic field pulse 504 are applied, so as to add positional information in the slice-direction and in the phase-encoding direction, to a phase of the magnetization.

After applying a readout gradient magnetic field pulse 505 for dephasing, which disperses the phase of nuclear magnetization within a pixel, nuclear magnetic resonance signals (echoes) 510, 511, 512, and 513 are measured, along with applying readout gradient magnetic field pulses 506, 507, 508, and 509 for adding positional information in the readout direction. And finally, a slice encoding gradient magnetic field pulse 514 and a phase encoding gradient magnetic field pulse 515 for rephasing are applied, for convergence of the phase of nuclear magnetization that has been dephased by the slice encoding gradient magnetic field pulse 503 and the phase encoding gradient magnetic field pulse 504.

The measurement controller 310 executes the procedures above, repeatedly every repetition time TR, while varying strength of the slice encoding gradient magnetic field pulses 503 and 514 (slice-encoding count ks) and of the phase encoding gradient magnetic field pulses 504 and 515 (phase-encoding count kp), and the phase of the RF pulse 502, whereby echoes necessary for acquiring one image are measured as to each echo time. In this situation, the phase of the RF pulse 502 may be incremented by 117 degrees, for instance. In FIG. 5, the numbers following the hyphen indicate the number of repetitions.

In each measured echo, a Flow Compensation gradient magnetic field pulse may be applied to each axis for compensating for an impact of flow such as bloodstream.

The measured echoes are arranged in three-dimensional k-space (memory space) having kr, kp, and ks as coordinate axes. In this situation, one echo occupies one line that is parallel to the kr axis in k-space. An absolute value image obtained by this RSSG sequence 550 may become a T1 (longitudinal relaxation time) weighted image for the echo with a short TE, whereas it may become a T2* weighted image where the phase dispersion within the pixel is reflected for the echo with a long TE.

The RSSG sequence 550 is taken as an example here, which is one method of Cartesian imaging for acquiring data in parallel to the coordinate axes in k-space. In the present embodiment, however, any sequence may be employed to acquire data in any k-space domain. For example, non-Cartesian imaging may be employed, such as radial scanning for acquiring data in k-space in rotational manner. A k-space scanning method (multi-echo planar imaging method) of echo-planar type using a plurality of TEs may also be applicable.

It is further possible to employ a sequence that creates one complex image and phase distribution, from different complex images and phase distributions acquired at a plurality of TEs. For example, if there is employed a pulse sequence that allows implementation of Dixon method for acquiring an image from signals obtained at a plurality of TEs, a frequency distribution representing static magnetic field inhomogeneity and an offset phase distribution can be obtained through the process of separating water from fat, for instance.

[Image Reconstruction: S1002]

Next, the image reconstructor 320 places in k-space the echo signals of at least two different echo times $TE_n$ (n is integer at least one, indicating the echo number) measured in step S1001, and applies Fourier transform to the echo signals. Accordingly, the image reconstructor 320 calculates, with respect to each TE, complex images I(n) where each pixel is a complex number.

[Local Frequency Distribution Calculation Process: S1003]

Next, the local frequency distribution calculator 330 calculates a local frequency distribution from the complex images I(n) reconstructed by the image reconstructor 320. The local frequency distribution represents local frequency changes caused by a magnetic susceptibility difference between living tissues, and this local frequency distribution is necessary for calculating a quantitative susceptibility distribution or a susceptibility weighted image with the application of the QSM method or the SWI method.

Prior to describing a specific method for calculating the local frequency distribution, a relationship between the complex image and the local frequency distribution will be described.

As described above, the complex image is obtained by reconstructing an image every TE on the basis of echoes measured at different TEs, and the complex image includes an absolute value component and a phase component (phase distribution). In the local frequency distribution calculation process of the present embodiment, the phase distribution is used to calculate the local frequency distribution.

Assuming the number of TE is N, the phase distribution P(n) of the complex image I(n) that is measured at the n-th TE may be broken down into the components as shown in the following formula 1:

[Formula 1]

$$P(n) = P_{inhomo}(n) + P_{offset} \quad (1)$$

where $P_{inhomo}$ is a phase distribution resulting from static magnetic field inhomogeneity due to causes such as a magnetic susceptibility difference between living tissues and a shape of the subject, and $P_{offset}$ is an offset phase distribution including phases such as a reception phase and a transmission phase that may occur upon measurement.

The phase distribution $P_{inhomo}$ caused by the static magnetic field inhomogeneity includes a local phase distribution caused by the local magnetic field changes arisen from a magnetic susceptibility difference between living tissues, and a global phase distribution (also referred to as a "background phase distribution") arisen from the shape of the subject, or the like. Therefore, $P_{inhomo}$ can be broken down into the components as shown in the formula 2:

[Formula 2]

$$P_{in\ hom\ o}(n) = P_{local}(n) + P_{global}(n) \quad (2)$$

where $P_{local}$ is the local phase distribution caused by the magnetic susceptibility difference between living tissues, and $P_{global}$ is the global phase distribution caused by the global magnetic field changes arisen from the shape of the subject, and the like.

On the other hand, phase P and frequency F in the complex image have a predetermined relationship (P=2πF× TE), and the local phase distribution $P_{local}$ and the global phase distribution $P_{global}$ are represented by the formulas 3 and 4, respectively, by using $TE_n$ (indicating n-th TE).

[Formula 3]

$$P_{local}(n) = 2\pi F_{local} TE_n \quad (3)$$

[Formula 4]

$$P_{global}(n) = 2\pi F_{global} TE_n \quad (4)$$

where $F_{local}$ is a local frequency distribution caused by local magnetic field changes arisen from the magnetic susceptibility difference between living tissues, and $F_{global}$ is a global frequency distribution caused by the global magnetic field changes arisen from the shape of the subject, and the like. In the following descriptions, a sum of the $F_{local}$ and the $F_{global}$ is represented as $F_{inhomo}$, which is referred to as a frequency distribution representing static magnetic field inhomogeneity. Thus, it is found that calculation of the offset phase distribution and the global frequency distribution according to the foregoing formulas 1 to 4 allows obtainment of the local frequency distribution.

According to the formulas 1 to 4, the local frequency distribution calculator 330 calculates the local frequency distribution $F_{local}$ from the phase distributions P(n) of the multi-echo complex images that are measured by the GrE method. At this time, a computation load in calculating the local frequency distribution can be reduced without lowering the SNR.

Figure 6:
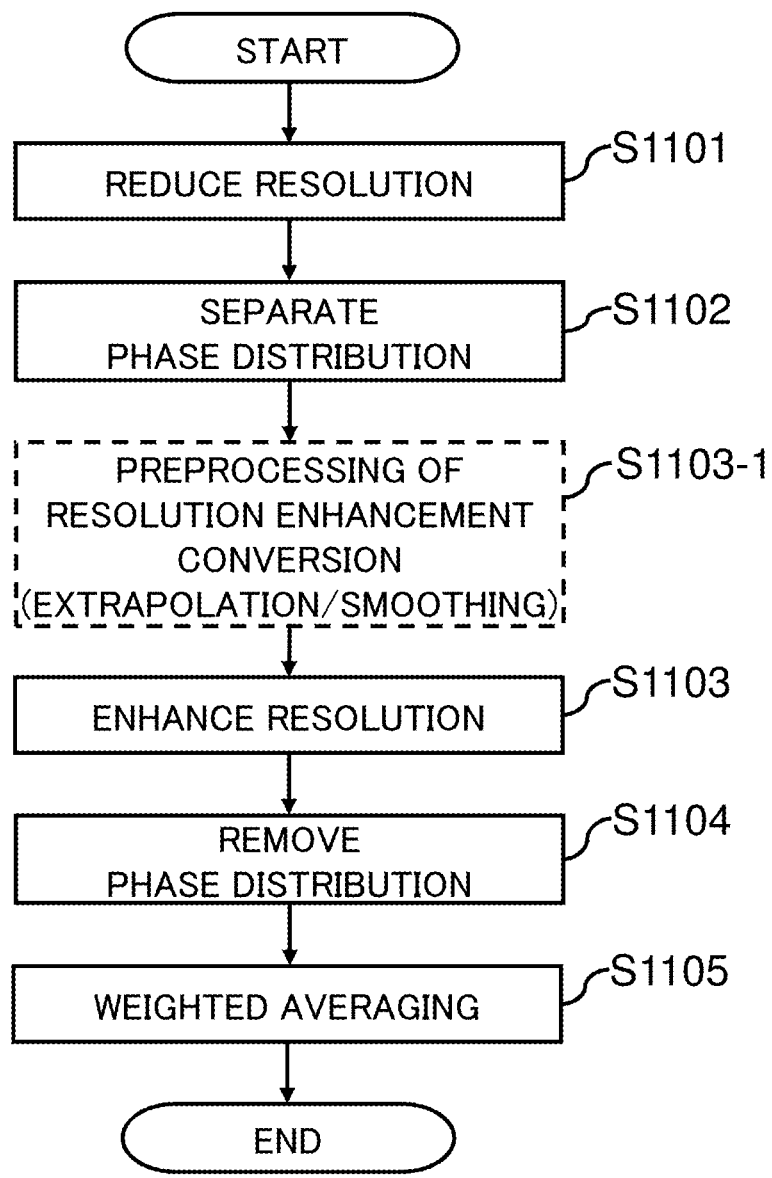
FIG. 6 is a flowchart of a process for calculating a local frequency distribution according to the first embodiment.

FIG. 6 shows details of the process (S1003) performed by the local frequency distribution calculator 330 according to the present embodiment. As illustrated, the local frequency distribution calculator 330 firstly converts the complex images I(n) into the complex images i(n) with resolution lower than the original resolution (low-resolution complex images i(n)) (S1101). Then, a low-frequency global frequency distribution $f_{global}$ and a low-frequency offset phase distribution $p_{offset}$ are separated from the low-resolution complex images i(n) (S1102). Next, the low-resolution global frequency distribution $f_{global}$ and the low-resolution offset phase distribution $p_{offset}$ are enhanced in resolution, so that the resolution becomes the same resolution level as that of the measured complex images I(n), whereby the global frequency distribution $F_{global}$ and the offset phase distribution $P_{offset}$ are obtained (S1103). Thereafter, by removing the global frequency distribution $F_{global}$ and the offset phase distribution $P_{offset}$ from thus measured complex images I(n), the local frequency distributions $F_{local}(n)$ of respective echoes are calculated (S1104). Then, a final single local frequency distribution $F_{local}$ is obtained by applying weighted averaging to the local frequency distributions $F_{local}(n)$ of the respective echoes (S1105).

Each component of the local frequency distribution calculator 330 as shown in FIG. 3 allows implementation of such processing as described above. That is, as illustrated, the local frequency distribution calculator 330 includes, a low-resolution converter (first resolution converter) 331 configured to convert complex images I(n) into complex images i(n), a phase distribution separator 332 configured to separate a low-resolution global frequency distribution $f_{global}$ and a low-resolution offset phase distribution $P_{offset}$ from the complex images i(n), a high-resolution converter (second resolution converter) 333 configured to enhance the resolution of the low-resolution global frequency distribution $f_{global}$ and of the low-resolution offset phase distribution $p_{offset}$ so that they have the same resolution as the complex images I(n) being measured, thereby calculating the global frequency distribution $F_{global}$ and the offset phase distribution $P_{offset}$, a phase remover 334 configured to remove the global frequency distribution $F_{global}$ and the offset phase distribution $P_{offset}$ from the complex images I(n) being measured and to calculate the local frequency distributions $F_{local}(n)$ of respective echoes, and a weighted averaging unit 335 configured to apply weighted averaging to the local frequency distributions $F_{local}(n)$ of respective echoes, so as to obtain a final single local frequency distribution $F_{local}$.

With reference to FIG. 6, there will now be described processing details performed by each component of the local frequency distribution calculator 330 according to the present embodiment.

[Reduction of Resolution: S1101]

The low-resolution converter 331 employs a publicly known method such as linear interpolation and Cubic interpolation for converting the resolution of the measured multi-echo complex images I(n) to desired resolution that is equal to or lower than the resolution of the measured multi-echo complex images I(n), whereby the complex images i(n) are calculated. The low-resolution converter 331 may also calculate the complex images i(n) with any converted resolution depending on a region, such as lower resolution inside the subject and higher resolution on the edge thereof, in accordance to a structure of the measured subject. It is alternatively possible to calculate the complex images i(n) with a plurality of resolution levels.

[Separation of Phase Distribution: S1102]

The phase distribution separator 332 separates the low-resolution global frequency distribution $F_{global}$ and the low-resolution offset phase distribution $p_{offset}$ from the low-resolution complex images i(n). Some methods may be available for this separation process, for example, a method that obtains a phase difference to acquire a phase difference image where the offset phase distribution has been removed, separates the global frequency distribution $f_{global}$ from this phase difference image, and further uses the low-resolution complex images i(n) and the global frequency distribution $f_{global}$ to separate the offset phase distribution $p_{offset}$; and a method that calculates at one time, the low-resolution global frequency distribution $f_{global}$ and the low-resolution offset phase distribution $p_{offset}$, according to a fitting using a signal logical expression. Those methods of this separation process will be described specifically in other embodiments.

[Enhancement of Resolution: S1103]

The high-resolution converter 333 employs publicly known methods, such as linear interpolation and Cubic interpolation, for enhancing the resolution of the low-resolution global frequency distribution $f_{global}$ and the low-resolution offset phase distribution $p_{offset}$ to a level equal to the resolution of the measured multi-echo complex images I(n), thereby calculating the global frequency distribution $F_{global}$ and the offset phase distribution $P_{offset}$.

It is to be noted that as surrounded by the dotted line in FIG. 6 (pre-processing of resolution enhancement conversion S1103-1), prior to enhancing the resolution of the low-resolution global frequency distribution $f_{global}$ and the low-resolution offset phase distribution $P_{offset}$, the edge of each low-resolution image may be extrapolated in advance. In other words, some edge information may be missing in the low-resolution image, and thus if the resolution enhancement is performed, keeping the image as it is, discontinuity (breaks) may occur in the high-resolution image. Subjecting the edge information to extrapolation with adjacent pixels may prevent such discontinuity. The extrapolation method is not limited particularly, but various methods are applicable such as polynomial fitting, in addition to the linear interpolation and Cubic interpolation.

It is further possible to remove noise via smoothing process, prior to enhancing resolution of the low-resolution global frequency distribution $f_{global}$ and the low-resolution offset phase distribution $p_{offset}$ (a function of smoothing unit). Any smoothing methods may be applicable, including various methods such as an average value filter with any window size, and a Gaussian filter. Usually, $f_{global}$ and $p_{offset}$ vary gently, and thus the smoothing process facilitates improvement of the SNR.

[Phase Removal: S1104]

The phase remover 334 removes the global frequency distribution $F_{global}$ and the offset phase distribution $P_{offset}$ from the measured complex images I(n), thereby calculating the local frequency distributions $F_{local}(n)$ of respective echoes. The local frequency distributions $F_{local}(n)$ of respective echoes can be calculated according to the following formulas 5 to 7.

Firstly, the formula 5 expresses the measured complex images I(n), using the local frequency distributions $F_{local}(n)$ of respective echoes, the global frequency distribution $F_{global}$, and the offset phase distribution $P_{offset}$.

[Formula 5]

$$I(n)kM_0 \exp\{j2\pi F_{local}(n)TE_n\}\exp(j2\pi F_{global}TE_n)\exp(jP_{offset}) \quad (5)$$

where j is imaginary number, $M_0$ is proton density, and k is a coefficient that depends on a measurement sequence. Therefore, the formula 6 expresses that the complex images I'(n) are obtained from the measured complex images I(n), through complex division of the global frequency distribution $F_{global}$ and a phase shift according to the offset phase distribution $P_{offset}$:

[Formula 6]

$$I'(n)=I(n)\exp(-j2\pi F_{global}TE_n)\exp(-jP_{offset})=kM_0 \exp\{j2\pi F_{local}(n)TE_n\} \quad (6)$$

As indicated by the Formula 7, phase components of the complex images I'(n) are taken to be converted into frequency components, thereby calculating the local frequency distributions $F_{local}(n)$ of respective echoes:

[Formula 7]

$$F_{local}(n) = \frac{\arg\{I'(n)\}}{2\pi TE_n} \quad (7)$$

[Weighted Averaging: S1105]

The weighted averaging unit 335 applies weighted averaging as indicated by the formula 8, to the local frequency distributions $F_{local}(n)$ of respective echoes calculated in S1104, whereby a final single local frequency distribution $F_{local}$ can be obtained:

[Formula 8]

$$F_{local} = \sum_{n=1}^{N} w(n)F_{local}(n) \quad (8)$$

where w(n) is a weight used for the weighted averaging, and it can be preset in the weighted averaging unit 335 or in the storage unit within the computer 109. The weight w(n) may be expressed by the formula 9, for instance, using the absolute value components |I(n)| of the complex images I(n) and echo times $TE_n$:

[Formula 9]

$$w(n) = \frac{TE_n|I(n)|}{\sum_{n=1}^{N} TE_n|I(n)|} \quad (9)$$

It is to be noted that the weight w(n) is not limited to the expression of the formula 9. As indicated by the formula 10, an apparent transverse magnetization relaxation rate $R_2^*$ (a reciprocal of transverse relaxation time $T_2^*$) may be used instead of the absolute value components |I(n)|.

[Formula 10]

$$w(n) = \frac{TE_n\exp(-R_2^*TE_n)}{\sum_{n=1}^{N} TE_n\exp(-R_2^*TE_n)} \quad (10)$$

According to the procedures as described above, the local frequency distribution $F_{local}$ can be calculated. In other words, the processing in the step S1003 (local frequency distribution calculation process) of FIG. 4 is completed.

According to the procedures above, the global frequency distribution $f_{global}$ and the offset phase distribution $p_{offset}$ can be calculated without using signal fitting. Therefore, this reduces the computation time as compared to the signal fitting described in the Non Patent Document 1 (conventional method 1). In addition, results obtained as to each complex image are subjected to weighted averaging thereby calculating the global frequency distribution $f_{global}$ and the offset phase distribution $p_{offset}$ accurately. According to the present embodiment, only one-time global frequency distribution calculation process is sufficient, which takes the computation time, and thus the computation time can be reduced as compared to the individual processing method (conventional method 2) as described in the Patent Document 1. In addition, since the global frequency distribution $f_{global}$ is calculated after separating the offset phase distribution $p_{offset}$, accuracy in calculating the global frequency distribution $f_{global}$ is improved.

[Calculation of Distribution Image: S1004]

Figure 7:
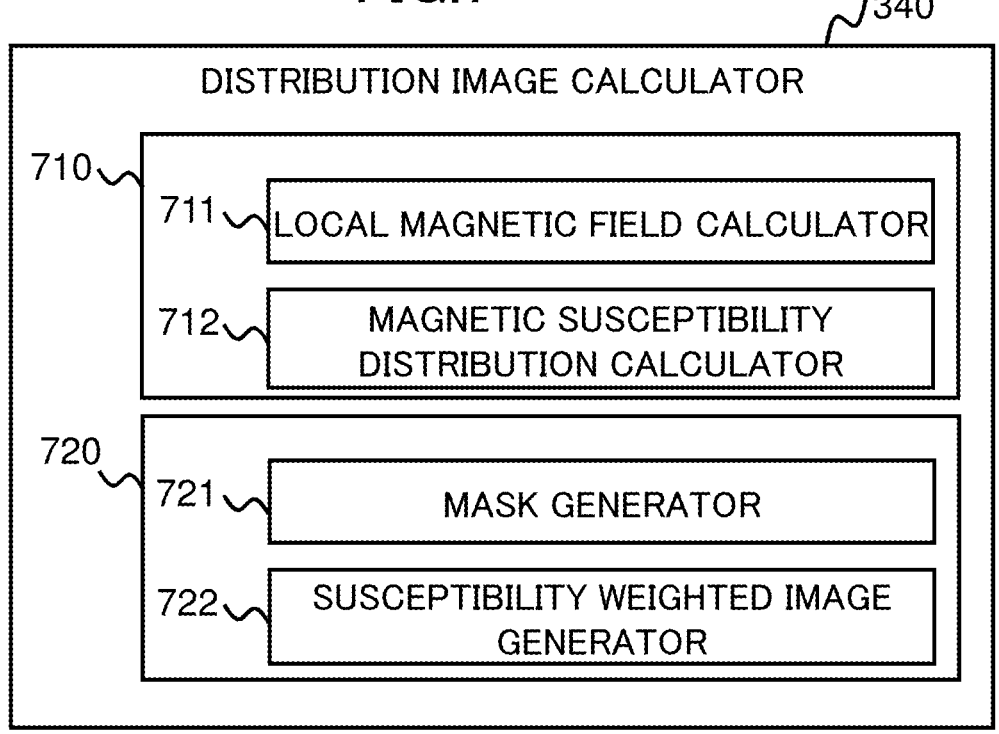
FIG. 7 is a functional block diagram of a distribution image calculator according to the first embodiment.

Referring to FIG. 4 again, processing performed by the distribution image calculator 340 (S1004) will be described. Distribution images may include, a magnetic field distribution, a quantitative susceptibility distribution, and a susceptibility weighted image, for example, and they may be obtained from the local frequency distribution $F_{local}$ calculated in S1003, according the QSM method or the SWI method. FIG. 7 is a functional block diagram showing the distribution image calculator 340 that performs the processing above.

As illustrated, the distribution image calculator 340 includes a quantitative susceptibility distribution calculator 710 and a susceptibility weighted image calculator 720, or either one of those calculators may be included. The quantitative susceptibility distribution calculator 710 comprises a local magnetic field calculator 711 configured to calculate a local magnetic field distribution by using the local frequency distribution calculated by the local frequency distribution calculator 330, and a magnetic susceptibility distribution calculator 712 configured to calculate a magnetic susceptibility distribution by using the local magnetic field calculated by the local magnetic field calculator 711 and a relational expression between the magnetic field and the magnetic susceptibility. The susceptibility weighted image calculator 720 includes a mask generator 721 configured to use the local frequency distribution calculated by the local frequency distribution calculator 330 to generate a susceptibility weighting mask, and a susceptibility weighted image generator 722 configured to multiply the absolute value components of a plurality of complex images, by the susceptibility weighting mask generated by the mask generator 721, thereby generating a susceptibility weighted image.

There will now be described specific examples of the processing performed by the distribution image calculator 340, that is, calculation of the quantitative susceptibility distribution using the QSM method (processing of the quantitative susceptibility distribution calculator 710), and calculation of the susceptibility weighted image using the SWI method (processing of the susceptibility weighted image calculator 720).

[Method of Calculating the Quantitative Susceptibility Distribution using QSM Method]

In the QSM method, local magnetic field changes caused by a magnetic susceptibility difference between living tissues are calculated, and a relational expression between the magnetic field and the magnetic susceptibility is used to calculate a quantitative susceptibility distribution. Therefore, the local magnetic field calculator 711 firstly calculates the magnetic field changes by using the local frequency distribution $F_{local}$.

In using the local frequency distribution $F_{local}$ calculated as described above, relative magnetic field variation (magnetic field distribution) $\delta(r)$ that is caused by the magnetic susceptibility difference between tissues is expressed by the following formula 11, assuming a position vector as r:

[Formula 11]

$$\delta(r) = -\frac{2\pi F_{local}(r)}{\gamma \cdot B_0} \quad (11)$$

where $\gamma$ is a nuclear gyromagnetic ratio of proton, and $B_0$ is static magnetic field strength.

Subsequently, the magnetic susceptibility distribution calculator 712 uses the magnetic field distribution $\delta(r)$ (local magnetic field) and a relational expression between the magnetic field and the magnetic susceptibility, so as to calculate the magnetic susceptibility distribution. Here, the magnetic field distribution $\delta(r)$ is expressed by the following formula 12 using the magnetic susceptibility distribution $\chi(r)$ within a living body, according to the Maxwell's equations with regard to a static magnetic field:

[Formula 12]

$$\delta(r) = \frac{1}{4\pi} \int \chi(r') \frac{3\cos^2\alpha - 1}{|r' - r|} dr'^3 \quad (12)$$
$$= d(r) \otimes \chi(r)$$

where $\alpha$ is an angle made by the vector (r'-r) and the static magnetic field direction, and d(r) is a point-dipole magnetic field.

As indicated by the formula 12, the magnetic field distribution $\delta(r)$ is represented by a convolution integral of the magnetic susceptibility distribution $\chi(r)$ and the point-dipole magnetic field d(r). Therefore, both sides of the formula 12 are subjected to the Fourier transform, whereby the formula 12 is transformed to the following formula 13:

[Formula 13]

$$\Delta(k) = \left(\frac{1}{3} - \frac{k_z^2}{k_x^2 + k_y^2 + k_z^2}\right) \cdot X(k) \quad (13)$$
$$= D(k) \cdot X(k)$$

where k=($k_x$, $k_y$, $k_z$) indicates the position vectors in k-space, $\Delta(k)$, X(k), and D(k) are Fourier components, respectively of the magnetic field distribution $\delta(r)$, the magnetic susceptibility distribution $\chi(r)$, and the point-dipole magnetic field d(r).

As indicated by the formula 13, the Fourier component X(k) of the magnetic susceptibility distribution can be obtained by dividing the Fourier component $\Delta(k)$ of the magnetic field distribution by the Fourier component D(k) of the point-dipole magnetic field. However, according to the formula 13, the reciprocal of D(k) diverges near the region D(k)=0, and thus X(k) cannot be calculated directly.

This region where D(k)=0 is referred to as a magic angle, and this forms a reverse bi-cone region that has an apex angle approximately twice as large as 54.7° with respect to the magnetic field direction. Due to this magic angle, the QSM method that assumes the magnetic susceptibility distribution based on the magnetic field distribution results in an ill-conditioned inverse problem, and thus several solutions are suggested.

Representative methods for those solutions include, a method of iterating a smoothing process on the magnetic susceptibility distribution calculated from the magnetic field distribution, under the constraints based on the relational expression between the magnetic field and the magnetic susceptibility (the method described in the Japanese Patent Application No. 2014-228843 by the inventors of the present application), the TKD (Truncated-based K-space Division) method for calculating the magnetic susceptibility distribution according to computations in k-space of the magnetic field distribution and the point-dipole magnetic field, the Iterative SWIM (Susceptibility Weighted Imaging and Mapping) method that combines through iterative operations, the magnetic susceptibility distribution calculated by the TKD method, with the magnetic susceptibility distribution obtained by extracting a fine structure by threshold processing, and the MEDI (Morphology enabled dipole inversion) method that uses a regularized least squares method. The susceptibility weighted image calculator 720 of the present embodiment uses those methods above to calculate a quantitative susceptibility distribution. Any methods are applicable in the present embodiment for calculating the quantitative susceptibility distribution.

[Method Using the SWI Method to Calculate Susceptibility Weighted Image]

There will now be described a method performed by the susceptibility weighted image calculator 720 for calculating a susceptibility weighted image by the SWI method. In the present embodiment, firstly, the mask generator 721 generates a susceptibility-weighting mask that weights the magnetic susceptibility, based on the local frequency distribution $F_{local}$. Specifically, the weighting mask is generated for rendering values of frequencies equal to or less than any frequency $f_m$ to be 0, the frequencies higher than the frequency $f_m$ to be 1, and the frequencies between 0 and 1 are set to be the values obtained by linear connection therebetween.

Thereafter, in the susceptibility weighted image generator 722, the weighting mask is multiplied any number of times, and then, an absolute value component (absolute value image) of the complex image at any TE is multiplied by this weighted mask, whereby the susceptibility weighted image is calculated. It is to be noted here that a method of calculating the susceptibility weighted image according to the present embodiment is not limited to the methods as described above. Various publicly known methods may also be applicable.

[Display Image: S1005]

The quantitative susceptibility distribution and the susceptibility weighted image calculated by the distribution image calculator 340 may be displayed on the display 110 (FIG. 2). Alternatively, they may be stored in the external storage device 111 in the form of image data, to be displayed on a desired display device.

Figure 4:
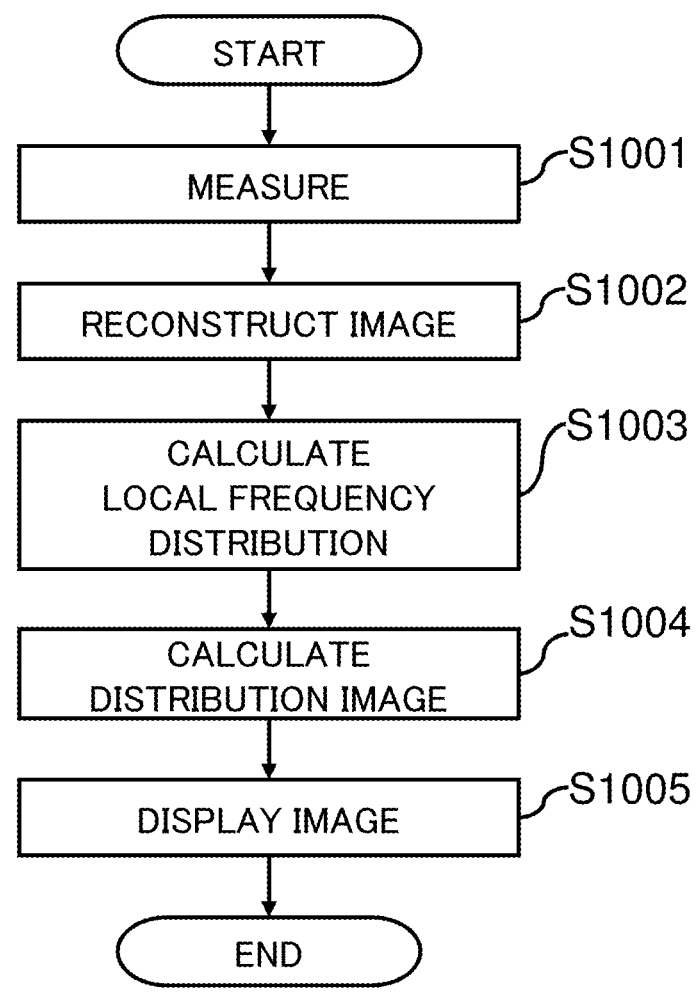
FIG. 4 illustrates a flowchart showing a process of the computer according to the first embodiment.

The flowcharts as shown in FIGS. 4 and 6 are just examples, and a part thereof may be omitted or another processing may be added thereto, within the scope of the present embodiment. By way of example, image displaying step S1005 in FIG. 4 may be omitted, and the weighted averaging step S1105 in FIG. 6 may be omitted, for example, in the case where the number of the complex images with different TEs is two.

There has been described so far a configuration of the MRI apparatus of the present invention and various processes performed by the computer thereof. The MRI apparatus of the present embodiment includes a transmitter configured to transmit an RF magnetic field pulse to a subject placed within a static magnetic field, a receiver configured to receive a nuclear magnetic resonance signal generated by the subject, a signal processor configured to process the nuclear magnetic signal received by the receiver and to generate measured data, and a computer configured to perform computations on the measured data that is generated by the signal processor, and the computer is provided with the functions to implement the following processing.

In other words, the computer according to the present embodiment converts multi-echo complex images measured at least two different echo times into low-resolution images. The computer separates, from a phase distribution of the low-resolution multi-echo complex images, a global frequency distribution caused by global magnetic field changes, and an offset phase distribution including phases such as a reception phase and a transmission phase. The computer enhances the resolution of thus obtained global frequency distribution and the offset phase distribution. The computer calculates local frequency distributions of respective echoes, from thus measured multi-echo complex images, the high-resolution global frequency distribution, and the high-resolution offset phase distribution. The computer applies weighted averaging to the local frequency distributions of respective echoes and calculates a final local frequency distribution.

Therefore, the computer includes, a first resolution converter configured to convert a plurality of complex image data items acquired by the MRI apparatus to lower resolution relative to the image data, a phase distribution separator configured to separate the global frequency distribution and the offset phase distribution from the low-resolution image that is processed by the first resolution converter, a second resolution converter configured to convert the resolution of the global frequency distribution and the resolution of the offset phase distribution separated by the phase distribution separator, to be the same level as the resolution of the plurality of image data items, and a local frequency distribution calculator configured to use the global frequency distribution and the offset phase distribution that are processed by the second resolution converter, and the plurality of image data items, so as to calculate a local frequency distribution.

Optionally, the computer of the present embodiment may be provided with a smoothing means or a means for extrapolating edge data, upon converting the low-resolution offset phase distribution and/or the low-resolution global frequency distribution into high-resolution distributions.

The computer provided with the aforementioned functions may be a part of the MRI apparatus, or may be an arithmetic processing unit, independent of the MRI apparatus. In other words, the present embodiment embraces not only the MRI apparatus, but also the computer (arithmetic processing unit) having the aforementioned functions.

According to the MRI apparatus (or the arithmetic processing unit) and the imaging processing method of the present embodiment, the local frequency distribution can be calculated easily with high precision, and using thus obtained local frequency distribution enables acquisition of desired distribution images, such as highly precise quantitative susceptibility distribution and susceptibility weighted image.

In view of thus described first embodiment, there will now be described the local frequency distribution calculator of the computer, in particular, specific embodiments of the functions of the phase distribution separator. Hereinafter, configurations and processing shown in FIGS. 1 to 6 that are referred to for describing the first embodiment are common <Second Embodiment>

In the present embodiment, upon separating the low-resolution global frequency distribution $f_{global}$ and the low-resolution offset phase distribution $p_{offset}$ from the low-resolution complex images i(n), the phase distribution separator 332 (FIG. 3) generates a phase difference image, obtains a frequency distribution representing static magnetic field inhomogeneity where the offset phase distribution has been eliminated, and then, separates the global frequency distribution $f_{global}$ from this frequency distribution representing static magnetic field inhomogeneity.

Figure 8:
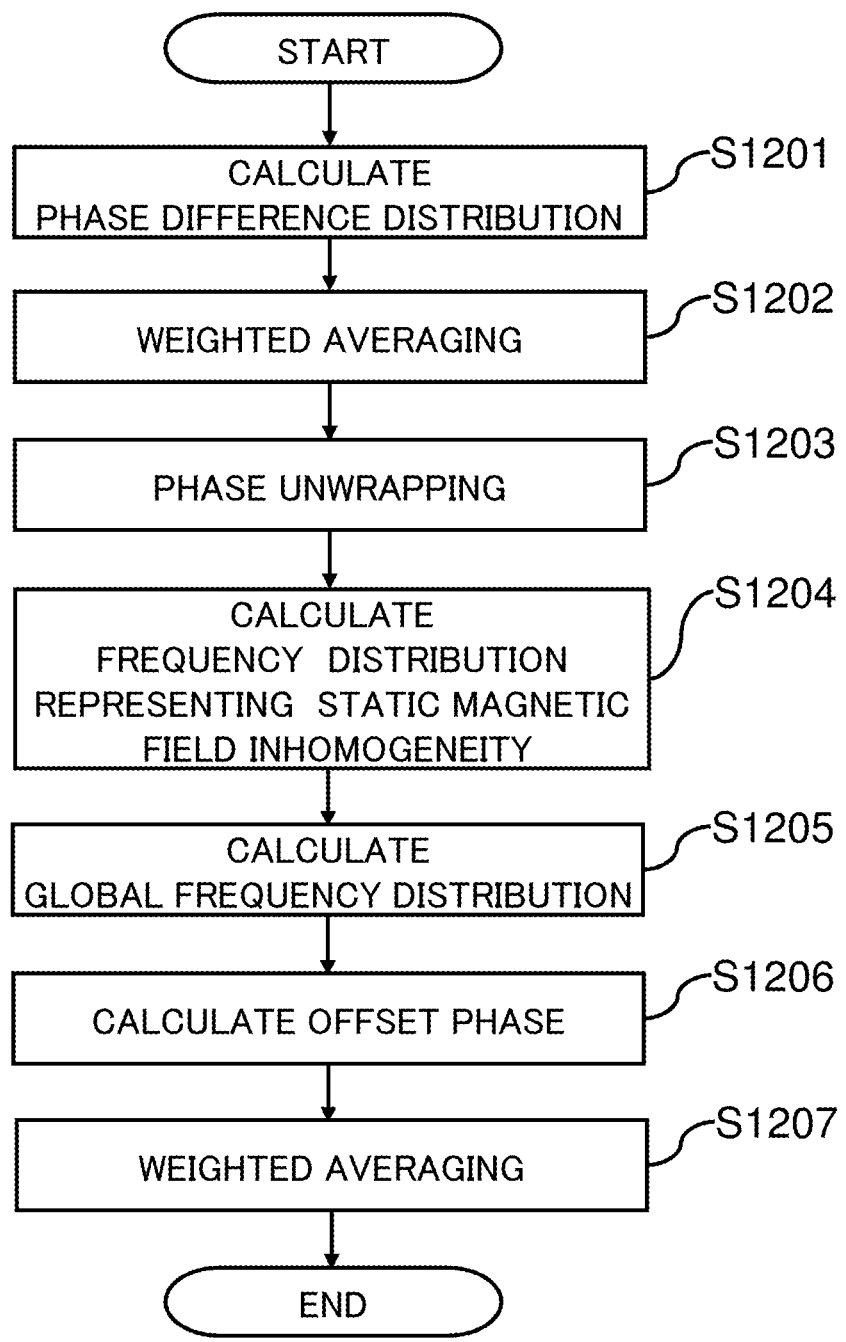
FIG. 8 is a flowchart showing a phase-distribution separation process according to a second embodiment.

As a precondition, also in the present embodiment, as shown in the flowchart of FIG. 6, the process of resolution reduction (S1101) is performed, and the processing such as the resolution enhancement (S1103) and the phase distribution removal (S1104) are performed, subsequent to the phase-distribution separation process (S1102). FIG. 8 illustrates an overview of the phase-distribution separation process (FIG. 6: S1102) of the present embodiment.

Firstly, the phase distribution separator 332 calculates (N−1) sets of the phase difference distributions Δp(n) between adjacent echoes, in the low-resolution complex images i(n) obtained by reducing the resolution of the complex images I(n) in the low-resolution converter 331 (S1201). Then, weighted averaging is applied to thus calculated phase difference distributions Δp(n), so as to obtain a single phase difference distribution Δp (S1202). A phase unwrapping process is performed on the phase difference distribution Δp (S1203) to be converted into a frequency component, and the frequency distribution representing static magnetic field inhomogeneity $f_{inhomo}$ is calculated (S1204). According to the global frequency distribution calculation process by separating the frequency distribution, the global frequency distribution $f_{global}$ is calculated from the frequency distribution representing static magnetic field inhomogeneity $f_{inhomo}$ (S1205). Phase shifts caused by the frequency distribution representing static magnetic field inhomogeneity $f_{inhomo}$ are removed from the low-resolution complex images i(TE$_n$), thereby calculating the offset phase distributions $p_{offset}$(n) of respective echoes (S1206). The weighted averaging is applied to the offset phase distributions $p_{offset}$(n) of respective echoes, and the offset phase distribution $p_{offset}$ is obtained (S1207). According to the procedures as described above, it is possible to calculate the low-resolution global frequency distribution $f_{global}$ and the low-resolution offset phase distribution $p_{offset}$ without using signal fitting.

Figure 9:
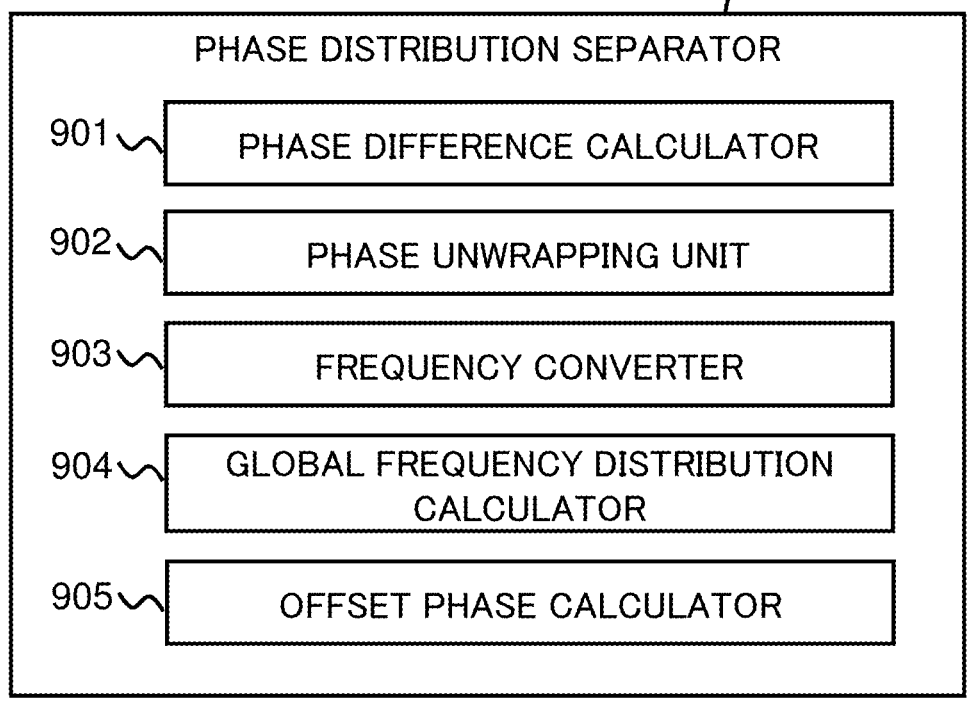
FIG. 9 is a functional block diagram of the phase-distribution separator according to the second embodiment.

FIG. 9 is a functional block diagram showing the phase distribution separator 332 for implementing the procedures above. As illustrated, the phase distribution separator 332 includes a phase difference calculator 901 configured to calculate (N−1) sets of the phase difference distributions Δp(n) between the adjacent echoes, a phase unwrapping unit 902 configured to perform a phase unwrapping process on the phase difference distribution Δp that is obtained by applying weighted averaging to the obtained phase difference distributions Δp(n), a frequency converter 903 configured to convert the phase difference component into a frequency component to calculate the frequency distribution representing static magnetic field inhomogeneity $f_{inhomo}$, a global frequency distribution calculator (frequency distribution separator) 904 configured to calculate the global frequency distribution $f_{global}$ from the frequency distribution representing static magnetic field inhomogeneity $f_{inhomo}$, and an offset phase calculator 905 configured to calculate the offset phase distributions $p_{offset}$(n) of respective echoes, by removing the phase shifts caused by the frequency distribution representing static magnetic field inhomogeneity $f_{inhomo}$ from the low-resolution complex images i(n).

With reference to FIG. 8, there will now be described details of the processing that are performed by each component in the phase distribution separator 332.

[Calculation of Phase Difference Distribution: S1201]

The phase difference calculator 901 calculates (N−1) sets of the phase difference distributions Δp(n) between adjacent echoes in the low-resolution multi-echo complex images i(n). Here, the low-resolution complex image i(n+1) at the (n+1)th echo time TE$_{n+1}$, and the low-resolution complex image i(n) at the n-th echo time TE$_n$ are expressed respectively by the formulas 14 and 15, using the low-resolution frequency distribution representing static magnetic field inhomogeneity $f_{inhomo}$ and the low-resolution offset phase distribution $p_{offset}$:

[Formula 14]

$$i(n+1)=k_{n+1}M_0 \exp(j2\pi f_{inhomo}TE_{n+1})\exp(jp_{offset}) \quad (14)$$

[Formula 15]

$$i(n)=k_n M_0 \exp(j2\pi f_{inhomo}TE_n)\exp(jp_{offset}) \quad (15)$$

Assuming the echo interval (echo time difference) between TE$_{n+1}$ and TE$_n$ as ΔTE$_n$, the complex ratio image Δi(n) obtained by through complex division of i(n+1) by i(n) are expressed by the formula 16:

[Formula 16]

$$\Delta i(n) = \frac{i(n+1)}{i(n)} = \frac{k_{n+1}}{k_n}\exp(j2\pi f_{inhomo}\Delta TE_n) \quad (16)$$

Therefore, the phase difference distribution Δp(n) between the adjacent echoes can be calculated according to the formula 17:

[Formula 17]

$$\Delta p(n)=\arg\{\Delta i(n)\}=2\pi f_{inhomo}\Delta TE_n \quad (17)$$

As indicated by the formulas 16 and 17, it is found that the phase difference distribution Δp(n) between adjacent echoes depends only on the phase shift according to the frequency distribution representing static magnetic field inhomogeneity $f_{inhomo}$ that is caused by static magnetic field inhomogeneity, where the low-resolution offset phase distribution $p_{offset}$ has been removed. In S1201, this processing is repeated (N−1) times, thereby calculating (N−1) sets of the phase difference distributions Δp(n) between the adjacent echoes.

[Weighted Averaging: S1202]

Next, in the weighted averaging unit 335, as indicated in the formula 18, the phase difference distributions Δp(n) between the adjacent echoes are subjected to weighted averaging, thereby calculating a single phase difference distribution Δp.

[Formula 18]

$$\Delta p = \sum_{n=1}^{N-1} w(n)\Delta p(n) \quad (18)$$

where w(n) is a weight, and any weight is applicable such as the weight used in the weighted averaging of the local frequency distributions $F_{local}$(n) of respective echoes (the weights as indicated in the formulas 9 and 10). The weighted averaging process in the weighted averaging unit 335 may also be a method that performs weighted averaging on the complex images, followed by calculating a phase component as indicated by the formula 19.

[Formula 19]

$$\Delta p = \arg\left\{\sum_{n=1}^{N-1} w(n)\Delta i(n)\right\} \quad (19)$$

According to this weighted averaging process, the SNR of the calculated phase difference distribution Δp is improved, thereby enhancing the precision of the processing as described below.

[Phase Unwrapping: S1203]

Next, in the phase unwrapping unit 902, the phase unwrapping process is executed on the phase difference distribution Δp, so as to remove the phase aliasing exceeding the range from −π to π. In a partial region in the phase difference distribution Δp, values exceeding the range from −π to π may be aliased into the range from −π to π. Therefore, in order to obtain an accurate phase in the entire region of the part to be imaged (e.g., a head part), it is necessary to correct such aliasing. In the present embodiment, by using an area expansion method, for example, such phase values aliased into the range from −π to π are corrected.

[Frequency Conversion: S1204]

Next, as indicated by the formula 20, the frequency converter 903 converts the phase difference distribution Δp into the frequency distribution representing static magnetic field inhomogeneity $f_{inhomo}$.

[Formula 20]

$$f_{inhomo} = \frac{\Delta p}{2\pi\Delta TE_n} \quad (20)$$

[Global Frequency Distribution Calculation (Frequency Distribution Separation): S1205]

Next, the global frequency distribution calculator 904 separates from the frequency distribution representing static magnetic field inhomogeneity $f_{inhomo}$, local frequency changes caused by a magnetic susceptibility difference between living tissues, or the like, and global frequency changes caused by a biological form, or the like, so as to calculate the global frequency distribution $f_{global}$.

As a typical method for calculating the global frequency distribution, there is a calculation method according to the Spherical Mean Value (SMV) filtering process, and this method is also applicable. The SMV filtering process utilizes that the global frequency distribution $f_{global}$ has a feature of spherical harmonics expansion. The spherical harmonics expansion has characteristics that a value at any point r is equal to an average value within the sphere having any radius surrounding the point r. The SMV filtering process uses the characteristics to calculate the global frequency distribution $f_{global}$.

The methods for calculating the global frequency distribution include, for example, in addition to the aforementioned methods, a method of calculating the global frequency distribution according to the least square method combining the aforementioned SMV filtering process with L2-norm regularization term, and a method of calculating the frequency distribution by the fitting using a three-dimensional image according to the low-order polynomial expression. Such methods as described above may also be applicable in the present embodiment.

[Offset Phase Calculation: S1206]

Next, the offset phase calculator 905 removes phase rotation caused by the frequency distribution representing static magnetic field inhomogeneity $f_{inhomo}$, from each echo image of the low-resolution multi-echo complex images i(n), thereby calculating the offset phase distributions $p_{offset}$(n) of respective echoes.

Assuming the complex images as i'(n) where the phase rotation caused by the frequency distribution representing static magnetic field inhomogeneity $f_{inhomo}$ is removed from the low-resolution multi-echo complex images i(n), i'(n) is expressed by the formula 21 using the formula 15.

[Formula 21]

$$i'(n)=i(n)\exp(-j2\pi f_{inhomo}TE_n)=k_n M_0 \exp\{jp_{offset}(n)\} \quad (21)$$

Therefore, the offset phase distribution $p_{offset}$(n) of each echo can be calculated by the formula 22:

[Formula 22]

$$P_{offset}(n)=\arg\{i'(n)\} \quad (22)$$

As indicated by the formulas 21 and 22, is found that the phase rotation caused by the frequency distribution representing static magnetic field inhomogeneity $f_{inhomo}$ has been removed from the phase components of the complex images i'(n).

[Weighted Averaging: S1207]

Next, as indicated by the formula 23, the weighted averaging unit 335 subjects the offset phase distributions $p_{offset}$(n) of respective echoes to weighted averaging, thereby calculating a single offset phase distribution $p_{offset}$.

[Formula 23]

$$p_{offset} = \sum_{n=1}^{N} w(n)p_{offset}(n) \quad (23)$$

where w(n) is a weight and any weight is applicable such as the weights in the aforementioned formulas 9 and 10. As indicated by the formula 24, it is also applicable to firstly perform weighted averaging on the complex images, followed by calculating the phase component.

[Formula 24]

$$p_{offset} = \arg\left\{\sum_{n=1}^{N} w(n)i'(n)\right\} \quad (24)$$

According to the weighted averaging process, the SNR of the offset phase distribution $p_{offset}$ is improved, and therefore calculation accuracy can be enhanced.

It is to be noted that in the processing flow as shown in FIG. 8, the steps S1205, S1206, and S1207 may be performed in any order. That is, after calculating the global frequency distribution (S1205), weighted averaging may be performed (S1207), followed by calculating the offset phase distribution (S1206).

The low-resolution global frequency distribution and the low-resolution offset phase distribution calculated by the phase-distribution separation process described so far, are converted to the distributions having the original resolution (FIG. 6: S1103), and then they are removed from the measured complex images I(n) (FIG. 6: S1104), whereby the local frequency distribution $f_{local}$ is calculated. Furthermore, by using the local frequency distribution, it is possible to acquire distribution images such as the magnetic field distribution, the quantitative susceptibility distribution, and the susceptibility weighted image (FIG. 4: S1004).

According to the present embodiment, similar to the first embodiment, separation of the offset phase distribution and the global frequency distribution is performed by using the distribution having less number of pixels with reduced resolution, and thus the computation time is shortened. In addition, the process for removing the global frequency distribution from the complex image can be performed, just by removing from the original complex image, the offset phase distribution and the global frequency distribution that have been separated at a low-resolution stage and resumed to be high resolution. Therefore, this allows further reduction of the computation time. Not only the global frequency distribution, but also the offset phase distribution can be also separated, the precision in the background removal processing (global frequency distribution removal) can be improved. In addition, weighted averaging is applied to the low-resolution offset phase distributions and the local frequency distributions, obtained with respect to each echo, the SNR of the finally acquired local frequency distribution can be enhanced.

Third Embodiment

As shown in FIGS. 8 and 9, in the aforementioned second embodiment, the phase distribution separator 332 firstly obtains a phase difference in the low-resolution complex images i(n), then, after removing the offset phase distribution, performs phase unwrapping and frequency conversion to calculate the low-resolution global frequency distribution, and further, calculates the low-resolution offset phase distribution.

In the present embodiment, the phase distribution separator 332 uses the signal fitting process, thereby separating at one time, the low-resolution global frequency distribution $f_{global}$ and the low-resolution offset phase distribution $p_{offset}$ from the low-resolution complex images i(n).

As indicated by the flowchart shown in FIG. 6, also in the present embodiment, the resolution reduction process (S1101) is performed, and subsequent to the phase-distribution separation process (S1102), the resolution enhancement process (S1103), the phase distribution removal process (S1104) and others are performed, similar to the first and the second embodiments.

Figure 10:
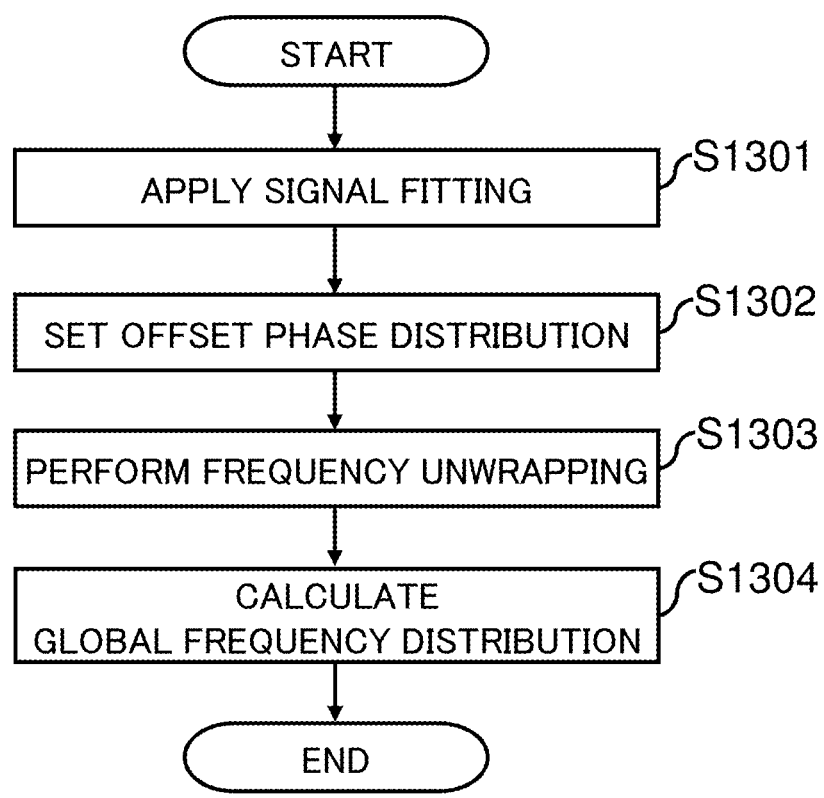
FIG. 10 is a flowchart of the phase-distribution separation process according to a third embodiment.
Figure 11:
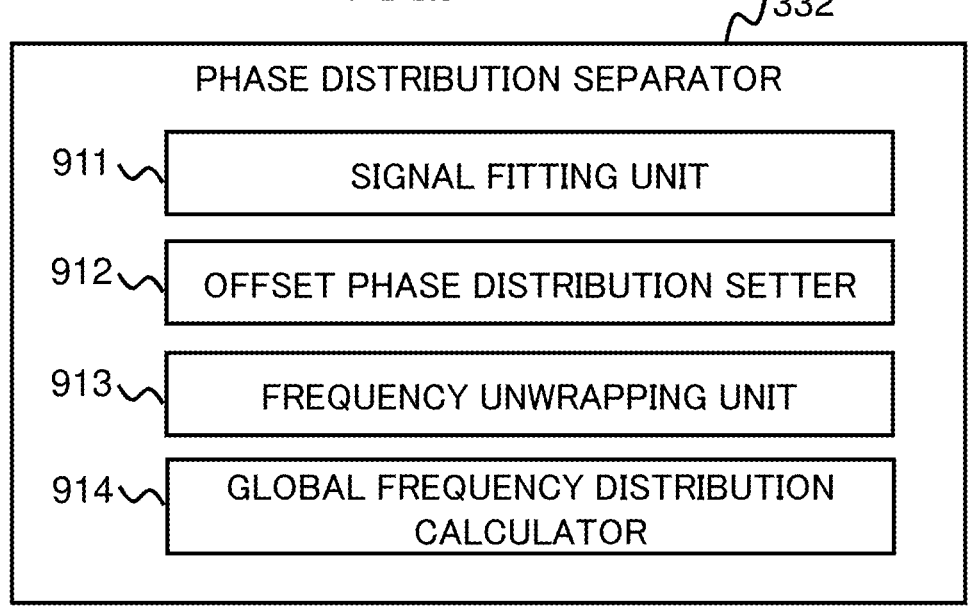
FIG. 11 is a functional block diagram of the phase-distribution separator according to the third embodiment.

With reference to FIGS. 10 and 11, there will be described the phase-distribution separation process (S1102) using the signal fitting process according to the present embodiment. FIG. 10 illustrates a processing overview of the phase distribution separator 332, and FIG. 11 is a functional block diagram showing functions of the phase distribution separator 332.

As shown in FIG. 10, the phase distribution separator 332 calculates the frequency distribution representing static magnetic field inhomogeneity $f_{inhomo}$ and the offset phase distribution $p_{offset}$, from the low-resolution complex images i(n) obtained by reducing the resolution of the complex images I(n) by the low-resolution converter 331, according to the fitting using the signal model of the GrE method (S1301). The offset phase component calculated by the signal fitting is set as the offset phase distribution $p_{offset}$ (S1302). Then, frequency unwrapping is applied to the frequency distribution representing static magnetic field inhomogeneity calculated by the signal fitting, thereby calculating the frequency distribution representing static magnetic field inhomogeneity $f_{inhomo}$ (S1303). Then, according to the global frequency distribution calculation process (frequency distribution separation process), the global frequency distribution $f_{global}$ is calculated from the frequency distribution representing static magnetic field inhomogeneity $f_{inhomo}$ to which frequency unwrapping has been applied (S1304). According to the procedures above, the low-resolution global frequency distribution $f_{global}$ and the low-resolution offset phase distribution $p_{offset}$ can be calculated respectively, without individual processing.

In order to implement the procedures above, as shown in FIG. 11, the phase distribution separator 332 of the present embodiment includes, a signal fitting unit 911 configured to fit the low-resolution complex images i(n) to a signal model of the GrE method by the signal fitting, an offset phase distribution setter 912 configured to set the offset phase component obtained by the signal fitting process as the offset phase distribution $p_{offset}$, a frequency unwrapping unit 913 configured to apply frequency unwrapping to the frequency distribution representing static magnetic field inhomogeneity calculated by the signal fitting, to calculate the frequency distribution representing static magnetic field inhomogeneity $f_{inhomo}$, and a global frequency distribution calculator 914 configured to calculate the global frequency distribution $f_{global}$ from the frequency distribution representing static magnetic field inhomogeneity $f_{inhomo}$ to which the frequency unwrapping has been applied.

With reference to FIG. 10, there will be described specific details performed by each component of the phase distribution separator 332 according to the present modification example.

[Fitting: S1301]

The signal fitting unit 911 fits the low-resolution complex images i(n) to the signal model of the GrE method by signal fitting. The signal model S(n) within a pixel measured by the GrE method is expressed by the formula 25:

[Formula 25]

$$S(n) = M_0 \exp(-R_2^* TE_n)\exp(j2\pi f_{inhomo} TE_n)\exp(jp_{offset}) \quad (25)$$

where $M_0$ is the proton density distribution within the pixel, and $R_2^*$ is an apparent transverse relaxation rate distribution.

By fitting the low-resolution multi-echo complex images i(n) to the signal model S(n) of the formula 25 according to the least squares fitting, the proton density distribution $M_0$, the apparent transverse relaxation rate distribution $R_2^*$, a temporary frequency distribution representing static magnetic field inhomogeneity $f_{inhomo}$, and the offset phase distribution $p_{offset}$ can be calculated. As the signal fitting, other than the least squares method, there may be employed a publicly known method such as the regularized least squares method, which is the least squares method to which a constrained term referred to as a regularization term is added.

[Offset Phase Distribution: S1302]

Next, in S1302, the offset phase distribution setter 912 sets the offset phase component obtained by the signal fitting process, as the offset phase distribution $p_{offset}$.

[Frequency Unwrapping: S1303]

The frequency unwrapping unit 913 applies frequency unwrapping to the temporary frequency distribution representing static magnetic field inhomogeneity $f_{inhomo}$ calculated by the signal fitting, thereby obtaining the frequency distribution representing static magnetic field inhomogeneity $f_{inhomo}$.

Assuming that the reciprocal of the echo interval (echo time difference) $\Delta TE$ as $f_{nyq}$, in a partial region of the temporary frequency distribution representing static magnetic field inhomogeneity $f_{inhomo}$, the frequency exceeding the range from $-f_{nyq}/2$ to $+f_{nyq}/2$ is aliased into the range from $-f_{nyq}/2$ to $+f_{nyq}/2$. A process for correcting this aliasing is referred to as frequency unwrapping, and in the present embodiment, the frequency aliased into the range from $-f_{nyq}/2$ to $+f_{nyq}/2$ is corrected by using a method such as an area expansion method. With such frequency unwrapping, it is possible to obtain an accurate phase in the entire region of the part to be imaged (e.g., the head part).

[Global Frequency Distribution Calculation: S1304]

Next, the global frequency distribution calculator 914 separates from the frequency distribution representing static magnetic field inhomogeneity $f_{inhomo}$, the local frequency changes and the global frequency changes caused by the biological form, and the like, thereby calculating the global frequency distribution $f_{global}$. The processing performed by the global frequency distribution calculator 914 is similar to the processing performed by the global frequency distribution calculator 904 according to the second embodiment (FIG. 8: S1205), and the SMV filtering process or other methods may also be employed.

According to the procedures above, the low-resolution global frequency distribution $f_{global}$ and the low-resolution offset phase distribution $P_{offset}$ can be calculated at one time. Then, the resolution of thus calculated low-resolution global frequency distribution and of the low-resolution offset phase distribution is converted to be equal to the resolution of the measured complex images (FIG. 6: S1103), and after they are removed from the measured complex images (FIG. 6: S1104), the local frequency distribution $f_{local}$ is calculated. Furthermore, by using this local frequency distribution, distribution images such as the magnetic field distribution, the quantitative susceptibility distribution, and the susceptibility weighted image can be acquired (FIG. 4: S1004).

According to the present embodiment, fitting is performed using the data with lowered resolution, and therefore, computation time can be reduced relative to a conventional fitting method. In addition, since the image has low resolution, noise is reduced and thus precision of the signal fitting is improved. According to the present embodiment, just one-time global frequency distribution calculation process is enough, which requires long computation time, and thus the computation time can be reduced relative to a conventional individual processing method. In addition, the global frequency distribution $f_{global}$ is calculated after separating the offset phase distribution $p_{offset}$, precision in calculating the global frequency distribution $f_{global}$ can be enhanced.

Fourth Embodiment

Next, there will be described a fourth embodiment of the present invention. The third embodiment relates to the case where a target substance is only one (e.g., only water signal). On the other hand, in the present embodiment, a target part contains in a mixed manner, a first substance (e.g., water signal), and a second substance (e.g., fat signal) that has a resonance frequency different from the first substance, and the local frequency distribution is calculated from the multi-echo complex images of at least two different TEs.

The MRI apparatus 100 used in the present embodiment has basically the same configuration as the first embodiment. Overviews of the processing as shown in FIGS. 4 and 6 are also common in the present embodiment, but the details of the phase-distribution separation process (FIG. 6: S1102) are different. There will now be described the present embodiment, focusing on a configuration of the phase distribution separator 332, which is different from the first embodiment.

Figure 12:
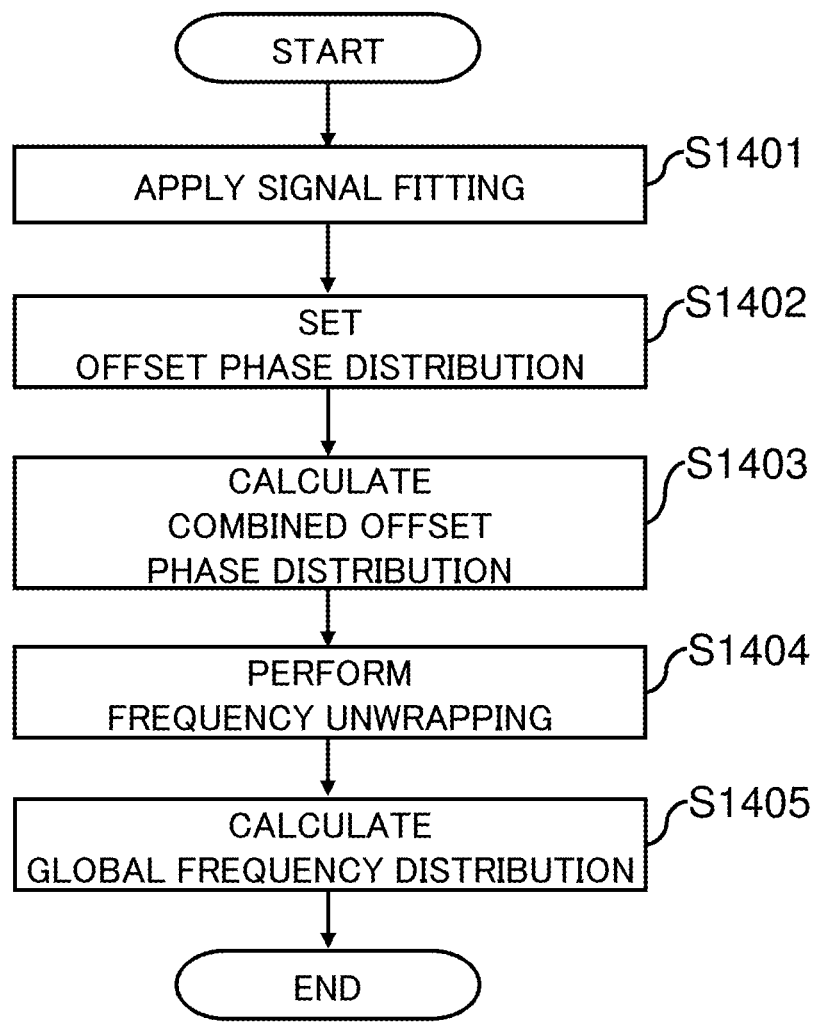
FIG. 12 is a flowchart showing the phase-distribution separation process according to a fourth embodiment.

With reference to FIG. 12, there will be described a phase-distribution separation process (S1102) employing a signal fitting process of the present embodiment. In the present embodiment, description will be made, assuming that the first substance is water, and the second substance is fat.

The phase distribution separator 332 calculates signal strength of water W and signal strength of fat F, the frequency distribution representing static magnetic field inhomogeneity $f_{inhomo}$, and a zero-order phase distribution, according to the fitting using the signal model of the GrE method, from low-resolution complex images i(n) obtained through resolution reduction of the complex images I(n) by the low-resolution converter 331 (S1401). Then, the zero-order phase component calculated by the signal fitting is set as the offset phase distribution $p_{offset}$ (S1402). The offset phase distribution $p_{offset}$ is combined with phase component $p_{fat}(n)$ that varies according to $TE_n$, caused by a frequency difference $F_{fat}$ between water and fat, thereby calculating combined offset phase distributions $p_{add}(n)$ (S1403). Then, the inhomogeneous static magnetic field frequency calculated by the signal fitting is subjected to frequency unwrapping, and the frequency distribution representing static magnetic field inhomogeneity $f_{inhomo}$ is obtained (S1404). The global frequency distribution $f_{global}$ is calculated from the frequency distribution representing static magnetic field inhomogeneity $f_{inhomo}$ after the frequency unwrapping is applied, through the global frequency calculation process (S1405). According to the procedures above, the low-resolution global frequency distribution $f_{global}$ and the low-resolution offset phase distribution $p_{offset}$ (including the phase difference $p_{fat}$ caused by the frequency difference between water and fat) can be calculated respectively.

Figure 13:
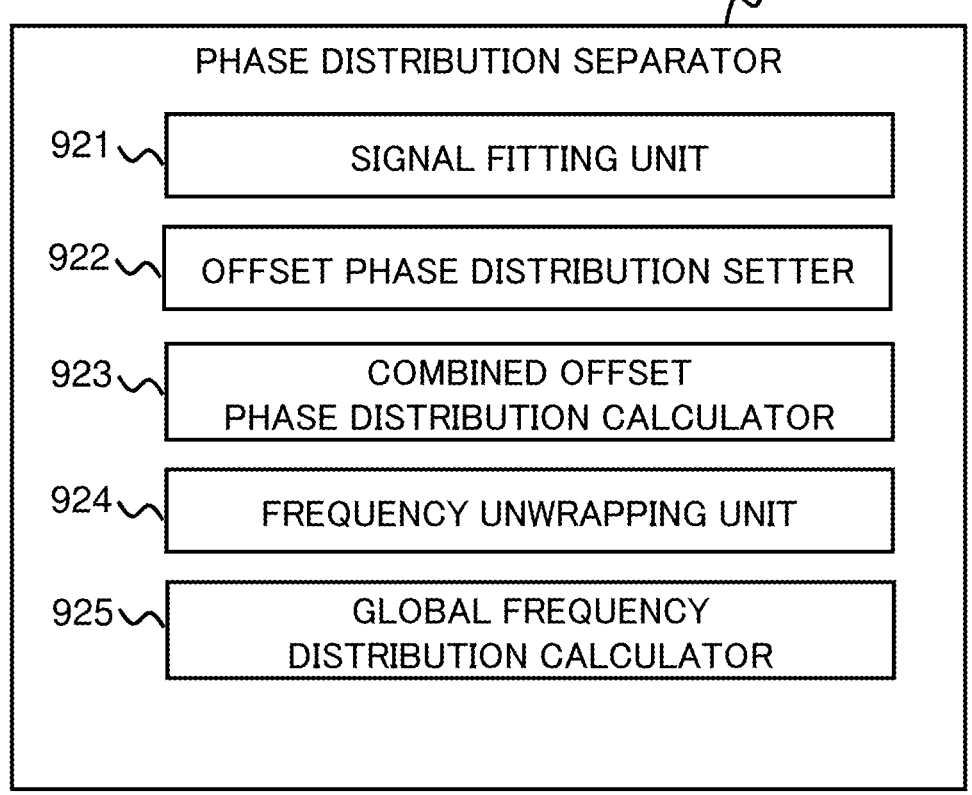
FIG. 13 is a functional block diagram of the phase-distribution separator according to the fourth embodiment.

In order to implement the features above, as illustrated in FIG. 13, the phase distribution separator 332 of the present embodiment includes, a signal fitting unit 921 configured to fit the low-resolution complex images i(n) by signal fitting, to the signal model of the GrE method including water and fat, an offset phase distribution setter 922 configured to set the offset phase component obtained by the signal fitting process, as the offset phase distribution $p_{offset}$, a combined offset phase distribution calculator 923 configured to combine the offset phase distribution $p_{offset}$ and the phase components $p_{fat}(n)$ caused by the frequency difference $f_{fat}$ between water and fat, and to calculate the combined offset phase distributions $p_{add}(n)$, a frequency unwrapping unit 924 configured to apply frequency unwrapping to the frequency distribution representing static magnetic field inhomogeneity calculated by the signal fitting to calculate the frequency distribution representing static magnetic field inhomogeneity $f_{inhomo}$, and a global frequency distribution calculator 925 configured to calculate the global frequency distribution $f_{global}$ from the frequency distribution representing static magnetic field inhomogeneity $f_{inhomo}$ to which frequency unwrapping has been applied, according to the global frequency distribution calculation process.

There will now be described each processing step shown in FIG. 12.

[Fitting: S1401]

Firstly in S1401, the signal fitting unit 921 applies fitting to the low-resolution complex images i(n), using the signal model of the GrE method, thereby calculating the frequency distribution representing static magnetic field inhomogeneity $f_{inhomo}$ and the offset phase distribution $p_{offset}$. The following formula 26 expresses the signal model S(n) within the pixel measured by the GrE method:

[Formula 26]

$$S(n) = \{W + F \exp(j2\pi f_{fat}TE_n)\}\exp(j2\pi f_{inhomo}TE_n)\exp(jP_{offset}) \quad (26)$$

where W is signal strength of water, F is the signal strength of fat, and $f_{fat}$ is a resonance frequency difference between water and fat, within the pixel.

With the least squares fitting to fit the measured low-resolution multi-echo complex images i(n) to the signal model S(n) as expressed by the formula 26, it is possible to calculate each of the followings within the pixel; the water signal strength W, the fat signal strength F, the temporary frequency distribution representing static magnetic field inhomogeneity $f_{inhomo}$, and the offset phase distribution $p_{offset}$. As the signal fitting, in addition to the least squares method, a publicly known method may be employed, such as the regularized least squares method, which is the least squares method to which a constrained term referred to as a regularization term is added. Furthermore, the term $\{W+F(j2\pi f_{fat}TE_n)\}$ in the formula 26 corresponds to the phase components $p_{fat}(n)$ caused by the resonance frequency difference $f_{fat}$ between water and fat, which can be calculated using W and F.

[Offset Phase Distribution Setting: S1402]

The offset phase distribution setter 922 sets the phase component obtained by the signal fitting process, as the offset phase distribution $p_{offset}$.

[Combined Offset Phase Distribution Calculation: S1403]

The phase components $p_{fat}(n)$ caused by the resonance frequency difference between water and fat are to be removed, like the offset phase distribution, so as to calculate the local frequency distribution $f_{local}$. Thus in S1403, as indicated by the formula 27, the combined offset phase distribution calculator 923 firstly calculates the phase distributions (referred to as combined offset phase distributions) $p_{add}(n)$, which is obtained by combining the offset phase distribution $p_{offset}$, with the phase components $p_{fat}(n)$ caused by the frequency difference $f_{fat}$ between water and fat.

[Formula 27]

$$P_{add}(n) = p_{fat}(n) + p_{offset} = \arg\{W + F \exp(j2\pi f_{fat}TE_n)\} + p_{offset} \quad (27)$$

[Frequency Unwrapping: S1404]

The frequency unwrapping unit 924 applies frequency unwrapping to the temporary frequency distribution representing static magnetic field inhomogeneity $f_{inhomo}$ calculated by the signal fitting, thereby calculating the frequency distribution representing static magnetic field inhomogeneity $f_{inhomo}$. The method of the frequency unwrapping is the same as that of the third embodiment, and the frequency component that exceeds the range from $-f_{nyq}/2$ to $+f_{nyq}/2$, being aliased into the range from $-f_{nyq}/2$ to $+f_{nyq}/2$, is corrected. Here, "$f_{nyq}$" represents the reciprocal of the echo interval (echo time difference) $\Delta TE$.

[Frequency Distribution Separation: S1405]

Next, the global frequency distribution calculator (frequency distribution separator) 925 separates from the frequency distribution representing static magnetic field inhomogeneity $t_{inhomo}$, the local frequency changes and the global frequency changes, caused by the biological form, or the like, so as to calculate the global frequency distribution $f_{global}$. This calculation method is the same as the processing of the global frequency distribution calculator (frequency distribution separator) 904 according to the second embodiment (FIG. 8: S1205), and the SMV filtering process or other methods may be employed.

According to the procedures above, it is possible to calculate the low-resolution global frequency distribution $f_{global}$, and the low-resolution combined offset phase distribution $p_{add}$ including the offset phase distribution $p_{offset}$ and the phase changes $p_{fat}$ caused by fat. Thereafter, the high-resolution converter 333 enhances the resolution of the low-resolution global frequency distribution $f_{global}$ and the low-resolution combined offset phase distribution $p_{add}$, then the phase remover 334 calculates the local frequency distribution of each echo, and then, the weighted averaging unit 335 calculates a final local frequency distribution.

Subsequently, as illustrated in FIG. 4, the phase-distribution separation process as shown in FIG. 12 converts thus calculated low-resolution global frequency distribution and the low-resolution combined offset phase distribution to an original resolution (FIG. 6: S1103), and thereafter such distributions are removed from the measured complex images I(n) (FIG. 6: S1104), so as to calculate the local frequency distribution $f_{local}$. Furthermore, by using the local frequency distribution, distribution images can be acquired, such as the magnetic field distribution, the quantitative susceptibility distribution, and the susceptibility weighted image (FIG. 4: S1004).

According to the present embodiment, even in a part containing water and fat in a mixed manner, the low-resolution global frequency distribution $f_{global}$ and the low-resolution offset phase distribution $P_{offset}$ can be calculated within a short time and with a high degree of precision. In addition, the phase component $p_{fat}$ caused by the resonance frequency difference between water and fat can also be calculated, which may become eventually unnecessary in obtaining the local frequency distribution. Therefore, a highly precise local frequency distribution can be calculated. Consequently, even in a target part containing water and fat in a mixed manner, it is possible to perform the QSM or SWI where impact of phase rotation due to fat has been eliminated.

DESCRIPTION OF SYMBOLS

100: MRI apparatus, 101: subject, 102: static magnetic field coil, 103: gradient coil, 104: shim coil, 105: transmitter coil, 106: receiver coil, 107: transmitter, 108: receiver, 109: computer, 110: display, 111: external storage device, 112: gradient magnetic field power supply, 113: shim power supply, 114: sequence controller, 115: input device, 120: MRI apparatus, 130: MRI apparatus, 310: measurement controller, 320: image reconstructor, 330: local frequency distribution calculator, 331: low-resolution converter (the first resolution converter), 332:phase distribution separator, 333: high-resolution converter (the second resolution converter), 334: phase remover, 335: weighted averaging unit, 340: distribution image calculator, 901: phase difference calculator, 902: phase unwrapping unit, 903: frequency converter, 904: global frequency distribution calculator (frequency distribution separator), 905: offset phase calculator, 911: signal fitting unit, 912: offset phase distribution setter, 913: frequency unwrapping unit, 914: global frequency distribution calculator (frequency distribution separator), 921: signal fitting unit, 922: offset phase distribution setter, 923: combined offset phase distribution calculator, 924: frequency unwrapping unit, 925: global frequency distribution calculator (frequency distribution separator)

What is claimed is:

1. A magnetic resonance imaging apparatus comprising,
a transmitter configured to transmit an RF magnetic field pulse to a subject placed within a static magnetic field,
a receiver configured to receive a nuclear magnetic resonance signal generated by the subject,
a gradient magnetic field generator configured to provide a gradient magnetic field to the static magnetic field, and
a computer configured to perform computations on the nuclear magnetic resonance signal thus received, wherein,
the computer comprising,
an image reconstructor configured to generate a plurality of complex images from the nuclear magnetic resonance signals acquired at a plurality of different echo times,
a first resolution converter configured to convert the plurality of complex images to low-resolution images having lower resolution than the complex images, respectively,
a phase distribution separator configured to separate a global frequency distribution and an offset phase distribution, from the low-resolution images processed in the first resolution converter,
a second resolution converter configured to convert the resolution of the global frequency distribution and of the offset phase distribution, separated by the phase distribution separator, to the same resolution as the plurality of the complex images, and
a local frequency distribution calculator configured to calculate a local frequency distribution, by using the global frequency distribution and the offset phase distribution processed in the second resolution converter.

2. The magnetic resonance imaging apparatus according to claim 1, wherein,
the phase distribution separator comprises,
a phase difference calculator configured to calculate a phase difference between the images, as to the plurality of the low-resolution images,
an aliasing remover configured to remove phase aliasing of the phase difference calculated by the phase difference calculator,
a frequency converter configured to calculate a frequency distribution, by converting the phase difference into a frequency, the phase aliasing of the phase difference having been removed by the aliasing remover,
a frequency distribution separator configured to separate the frequency distribution calculated by the frequency converter, into a global frequency distribution and a local frequency distribution, and
an offset phase distribution calculator configured to calculate an offset phase distribution, by using the low-resolution images and the frequency distribution calculated by the frequency converter.

3. The magnetic resonance imaging apparatus according to claim 1, wherein,
the phase distribution separator comprises,
a fitting unit configured to fit each of the plurality of the low-resolution images to a signal logical expression upon measurement, thereby calculating a frequency distribution and the offset phase distribution,
an aliasing remover configured to remove aliasing of the frequency distribution, and
a frequency distribution separator configured to separate the frequency distribution where the aliasing has been removed by the aliasing remover, into the global frequency distribution and the local frequency distribution.

4. The magnetic resonance imaging apparatus according to claim 1, wherein,
the phase distribution separator comprises,
a fitting unit configured to set a signal logical expression including a signal of a first substance and a signal of a second substance having a resonance frequency different from the first substance, and to fit each of the plurality of the low-resolution images to the signal logical expression, thereby calculating a phase distribution caused by a resonance frequency difference between the first substance and the second substance, a frequency distribution, and the offset phase distribution,
a frequency distribution separator configured to separate the frequency distribution calculated by the fitting unit, into the global frequency distribution and the local frequency distribution, and
a combined offset phase distribution calculator configured to combine the phase distribution caused by the resonance frequency difference, with the offset phase distribution, wherein,
the second resolution converter coverts the global frequency distribution and the combined offset phase distribution to have the same resolution as the plurality of complex images, and the local frequency distribution calculator uses the global frequency distribution, the combined offset phase distribution processed by the second resolution converter, and the plurality of complex images, so as to calculate the local frequency distribution.

5. The magnetic resonance imaging apparatus according to claim 4, wherein,
the first substance and the second substance are water and fat.

6. The magnetic resonance imaging apparatus according to claim 1, wherein,
the computer further comprises,
a weighted averaging unit configured to apply weight averaging to the global frequency distribution and/or the local frequency distribution calculated as to each of the plurality of complex images.

7. The magnetic resonance imaging apparatus according to claim 1, wherein, the second resolution converter comprises a smoothing unit configured to smooth the global frequency distribution and/or the offset phase distribution.

8. The magnetic resonance imaging apparatus according to claim 1, further comprising,
   a local magnetic field calculator configured to calculate a local magnetic field distribution, by using the local frequency distribution calculated by the local frequency distribution calculator, and
   a magnetic susceptibility distribution calculator configured to calculate a magnetic susceptibility distribution by using the local magnetic field calculated by the local magnetic field calculator, and a relational expression between a magnetic field and a magnetic susceptibility.

9. The magnetic resonance imaging apparatus according to claim 1, further comprising,
   a mask generator configured to generate a susceptibility weighting mask, by using the local frequency distribution calculated by the local frequency distribution calculator, and
   a susceptibility weighted image generator configured to multiply absolute value components of the plurality of complex images, by the susceptibility weighting mask generated by the mask generator.

10. The magnetic resonance imaging apparatus according to claim 1, wherein,
    the computer is provided in the form of an independent image processor.

11. An image processing method of calculating a local frequency distribution, by using a plurality of complex images acquired at different echo times according to a magnetic resonance imaging apparatus, comprising,
    converting the plurality of complex images respectively to image data items of low-resolution complex images with resolution lower than the plurality of complex images,
    separating a global frequency distribution and an offset phase distribution from the low-resolution complex images,
    converting the global frequency distribution and the offset phase distribution into high-resolution image data items with the same resolution as the image data items of the plurality of complex images, and
    calculating the local frequency distribution, by using the global frequency distribution and the offset phase distribution converted to high resolution, and the plurality of complex images.

12. An image processing method of calculating a local frequency distribution, by using a plurality of complex images acquired at different echo times according to a magnetic resonance imaging apparatus, comprising,
    converting the plurality of complex images respectively to image data items of low-resolution complex images with resolution lower than the plurality of complex images,
    setting a signal logical expression including a signal of a first substance and a signal of a second substance having a resonance frequency different from the first substance, and fitting each of the plurality of the low-resolution images to the signal logical expression, thereby calculating a phase distribution caused by a resonance frequency difference between the first substance and the second substance, a frequency distribution, and an offset phase distribution,
    separating the frequency distribution into a global frequency distribution and a local frequency distribution,
    combining the phase distribution caused by the resonance frequency difference, with the offset phase distribution, so as to calculate a combined phase distribution,
    converting the resolution of the global frequency distribution separated from the frequency distribution and of the combined phase distribution, to the same resolution as the resolution of the plurality of complex images, and
    calculating the local frequency distribution, by using the global frequency distribution and the combined phase distribution, converted to the same resolution as the resolution of the plurality of complex images, and the plurality of complex images.

* * * * *